United States Patent
Thompson, Jr. et al.

(10) Patent No.: US 9,744,755 B2
(45) Date of Patent: Aug. 29, 2017

(54) METHOD OF MAKING ABSORBENT FOAM COMPOSITES

(71) Applicant: 3M INNOVATIVE PROPERTIES COMPANY, St. Paul, MN (US)

(72) Inventors: Delton R. Thompson, Jr., Lake Elmo, MN (US); Timothy V. Stagg, Hudson, WI (US); Thomas R. LaLiberte, Inver Grove Heights, MN (US); Leigh E. Wood, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 529 days.

(21) Appl. No.: 13/854,371

(22) Filed: Apr. 1, 2013

(65) Prior Publication Data
US 2014/0295135 A1    Oct. 2, 2014

(51) Int. Cl.
*B32B 37/15* (2006.01)
*B32B 38/04* (2006.01)
(Continued)

(52) U.S. Cl.
CPC ........ *B32B 38/04* (2013.01); *A61F 13/15617* (2013.01); *A61F 13/534* (2013.01);
(Continued)

(58) Field of Classification Search
CPC ............ B32B 3/266; B32B 2038/0084; B29C 44/5663; B29C 44/362; B29C 42/22;
(Continued)

(56) References Cited

U.S. PATENT DOCUMENTS

| | | | |
|---|---|---|---|
| 2,957,207 A | 10/1960 | Roop et al. | |
| 3,258,511 A * | 6/1966 | McGregor, Jr. | 264/46.4 |

(Continued)

FOREIGN PATENT DOCUMENTS

| | | |
|---|---|---|
| CN | 201906098 U | 7/2011 |
| GB | 2 083 487 A | 3/1982 |

(Continued)

OTHER PUBLICATIONS

E-A-R Specialty Composites, "Economical, Single-Step Process Produces Urethane Foams", http://www.earsc.com/HOME/engineering/TechnicalWhitePapers/ThinSheetCasting/index.asp?SID=68, 2006, 1 page.

(Continued)

*Primary Examiner* — William Bell
(74) *Attorney, Agent, or Firm* — Steven Bern; Lynn R. Hunsberger

(57) ABSTRACT

A method of making absorbent foam composites and absorbent foam composites produced therefrom. The method comprises casting an absorbent foam layer having a first side and a second side opposite the first side onto a barrier layer having a first side and second side opposite the first side, where the second side of the absorbent foam layer is in contact with the first side of the barrier layer; joining a second absorbent layer to the second side of the barrier layer before, during, or after the casting step; and breaching the barrier layer after the casting step so that the foam layer and second absorbent layer are in fluid communication. The absorbent foam composites can be used in a variety of applications, including personal hygiene articles, medical bandages, pet pads and agricultural pads.

11 Claims, 3 Drawing Sheets

(51) Int. Cl.
 *A61F 13/534*   (2006.01)
 *B32B 3/26*   (2006.01)
 *A61F 13/15*   (2006.01)
 *B32B 5/18*   (2006.01)
 *B32B 5/24*   (2006.01)
 *B32B 27/12*   (2006.01)
 *B32B 3/12*   (2006.01)
 *B32B 37/26*   (2006.01)
 *B32B 38/00*   (2006.01)
 *A61F 13/53*   (2006.01)

(52) U.S. Cl.
 CPC ............... *B32B 3/12* (2013.01); *B32B 3/266* (2013.01); *B32B 5/18* (2013.01); *B32B 5/24* (2013.01); *B32B 27/12* (2013.01); *A61F 2013/530802* (2013.01); *B32B 2037/268* (2013.01); *B32B 2038/0084* (2013.01); *B32B 2038/045* (2013.01); *B32B 2038/047* (2013.01); *B32B 2262/062* (2013.01); *B32B 2266/025* (2013.01); *B32B 2266/0257* (2013.01); *B32B 2266/0264* (2013.01); *B32B 2266/0278* (2013.01); *B32B 2307/726* (2013.01); *B32B 2375/00* (2013.01); *B32B 2556/00* (2013.01); *Y10T 428/24331* (2015.01); *Y10T 428/249953* (2015.04)

(58) Field of Classification Search
 CPC ... B29C 47/0042; B29C 44/32; B29C 44/321; A61F 2013/530817; A61F 2013/530839
 See application file for complete search history.

(56) References Cited

U.S. PATENT DOCUMENTS

| | | | |
|---|---|---|---|
| 3,874,964 A * | 4/1975 | Cogliano et al. | 156/78 |
| 3,941,633 A | 3/1976 | Wang et al. | |
| 4,394,930 A * | 7/1983 | Korpman | A61L 15/20 215/12.1 |
| 4,547,920 A * | 10/1985 | Hulsebusch et al. | 297/256 |
| 4,592,751 A * | 6/1986 | Gegelys | A61F 13/537 604/368 |
| 4,600,637 A | 7/1986 | Kafka et al. | |
| 4,610,678 A | 9/1986 | Weisman et al. | |
| 4,643,726 A | 2/1987 | Gegelys | |
| 4,783,287 A | 11/1988 | Eichberger et al. | |
| 5,093,175 A | 3/1992 | Goto et al. | |
| 5,110,843 A | 5/1992 | Bries et al. | |
| 5,227,245 A * | 7/1993 | Brands et al. | 428/483 |
| 5,254,301 A | 10/1993 | Sessions et al. | |
| 5,294,386 A * | 3/1994 | Roth et al. | 264/46.6 |
| 5,397,316 A * | 3/1995 | LaVon | A61F 13/535 604/358 |
| 5,785,697 A | 7/1998 | Trombetta et al. | |
| 5,798,064 A | 8/1998 | Peterson | |
| 5,899,893 A | 5/1999 | Dyer et al. | |
| 5,916,928 A | 6/1999 | Sessions et al. | |
| 6,140,550 A | 10/2000 | Beihoffer et al. | |
| 6,294,590 B1 | 9/2001 | Ragsdale et al. | |
| 6,403,857 B1 | 6/2002 | Gross et al. | |
| 6,410,820 B1 | 6/2002 | McFall et al. | |
| 6,852,905 B2 | 2/2005 | Baker | |
| 6,896,669 B2 | 5/2005 | Krautkramer et al. | |
| 6,915,741 B2 | 7/2005 | Price et al. | |
| 7,176,344 B2 | 2/2007 | Gustafson et al. | |
| 7,338,983 B2 | 3/2008 | Simpson et al. | |
| 7,670,517 B2 | 3/2010 | Tadokoro et al. | |
| 7,799,967 B2 * | 9/2010 | Ranganathan et al. | 604/369 |
| 2002/0137418 A1 * | 9/2002 | Seth | B32B 5/08 442/334 |
| 2003/0093050 A1 | 5/2003 | Baker | |
| 2004/0109992 A1 | 6/2004 | Gribble et al. | |
| 2004/0182499 A1 | 9/2004 | Collier | |
| 2009/0157021 A1 | 6/2009 | Sullivan et al. | |
| 2010/0267304 A1 | 10/2010 | Fowler | |
| 2010/0272955 A1 | 10/2010 | Chimelak et al. | |
| 2010/0316834 A1 | 12/2010 | Jokisch et al. | |
| 2011/0087184 A1 | 4/2011 | Woehlke et al. | |
| 2011/0087185 A1 | 4/2011 | Woehlke et al. | |
| 2011/0097536 A1 | 4/2011 | Jokisch et al. | |
| 2011/0137274 A1 | 6/2011 | Klofta et al. | |
| 2012/0029454 A1 | 2/2012 | Li et al. | |
| 2012/0034432 A1 * | 2/2012 | Cotton | A61F 13/15699 428/195.1 |
| 2012/0053547 A1 | 3/2012 | Schroeder et al. | |
| 2012/0095426 A1 | 4/2012 | Visscher et al. | |

FOREIGN PATENT DOCUMENTS

| | | |
|---|---|---|
| JP | 2011130799 A | 7/2011 |
| WO | WO 95/00091 | 1/1995 |
| WO | WO 2009/152021 A2 | 12/2009 |
| WO | WO 2011/115537 | 9/2011 |
| WO | WO 2013/180832 A1 | 12/2013 |
| WO | WO 2013/180937 A1 | 12/2013 |

OTHER PUBLICATIONS

Design U.S. Appl. No. 29/429,799, filed Aug. 16, 2012, entitled "Mechanical Fastener".
Design U.S. Appl. No. 29/429,801, filed Aug. 16, 2012, entitled "Mechanical Closure Element".
International Search Report for International Application No. PCT/US2014/032504, filed on Apr. 1, 2014, mailed on Jul. 17, 2014, 8 pages.
EP Search Report, EP 14 77 9837, mailed Jan. 27, 2017 (7 pages).

* cited by examiner

METHOD OF MAKING ABSORBENT FOAM COMPOSITES

FIELD OF INVENTION

The present invention relates to a method of making absorbent foam composites and absorbent foam composites produced therefrom. The absorbent foam composites can be used in a variety of disposable absorbent articles, including personal hygiene articles, medical bandages, pet pads and agricultural pads.

BACKGROUND

Disposable absorbent articles typically include an absorbent core sandwiched between a fluid impervious backsheet and a fluid pervious topsheet. The absorbent core can be a single material or a composite of two or more materials. Exemplary composite cores are described in U.S. Ser. No. 61/652,388 and U.S. Ser. No. 61/652,408, which were co-filed on May 29, 2012. The exemplary composites include a polymeric foam layer and a second absorbent layer. The layers are sufficiently proximate each other such that fluid from the absorbent foam layer is readily transported to the second absorbent layer.

SUMMARY

The present invention provides a method of making absorbent foam composites and absorbent foam composites produced therefrom In one embodiment, the invention provides a method of making an absorbent foam composite comprising casting an absorbent foam layer having a first side and a second side opposite the first side onto a barrier layer having a first side and a second side opposite the first side, where the second side of the absorbent foam layer is in contact with the first side of the barrier layer; joining a second absorbent layer to the second side of the barrier layer before, during, or after the casting step; and breaching the barrier layer after the casting step so that the absorbent foam layer and second absorbent layer are in fluid communication.

In another embodiment, the invention provides a method of making an absorbent foam composite comprising taking an intermediate composite comprising a barrier layer having a first side and a second side opposite the first side, an absorbent foam layer joined to the first side of the barrier layer, and a second absorbent layer joined to the second side of the barrier layer; and breaching the barrier layer so that the absorbent foam layer and second absorbent layer are in fluid communication.

In a further embodiment, the invention provides an absorbent foam composite comprising a barrier layer having a first side and a second side opposite the first side; an absorbent foam layer joined to the first side of the barrier layer; and a second absorbent layer joined to the second side of the barrier layer, where the barrier layer has been breached so that the absorbent foam layer and second absorbent layer are in fluid communication.

In yet a further embodiment, the invention provides a method of making an absorbent foam composite comprising casting an absorbent foam layer having a first side and a second side opposite the first side onto a barrier layer having a first side and a second side opposite the first side, where the second side of the absorbent foam layer is in contact with the first side of the barrier layer; joining a second absorbent layer to the second side of the barrier layer before, during, or after the casting step; adding a second barrier layer to the first side of the absorbent foam layer during the casting step, where the second barrier layer has a first side and a second side opposite the first side, and the second side of the second barrier layer is in contact with the first side of the absorbent foam layer; joining a third absorbent layer to the first side of the second barrier layer before, during or after the casting step; breaching the two barrier layers so that the absorbent foam layer is in fluid contact with each of the second and third absorbent layers; and skiving the foam layer to create two absorbent foam composites.

In yet another embodiment, the invention provides a method of making an absorbent foam composite comprising taking an intermediate composite comprising an absorbent foam layer having a first side and a second side opposite the first side, a barrier layer having a first side and a second side opposite the first side, where the first side of the barrier layer is joined to the second side of the absorbent foam layer, a second absorbent layer joined to the second side of the barrier layer, a second barrier layer joined to the first side of the absorbent foam layer, where the second barrier layer has a first side and a second side opposite the first side, and the second side of the second barrier layer is in contact with the first side of the absorbent foam layer, and a third absorbent layer joined to the first side of the second barrier layer, wherein the two barrier layers have been breached so that the foam layer is in fluid contact with each of the second and third absorbent layers; and skiving the absorbent foam layer to create two absorbent foam composites.

In yet a further embodiment, the invention provides an intermediate for making an absorbent foam composite comprising an absorbent foam layer having a first side and a second opposite the first side; a barrier layer having a first side and a second side opposite the first side, where the first side of the barrier layer is joined to the second side of the absorbent foam layer; a second absorbent layer joined to the second side of the barrier layer; a second barrier layer joined to the first side of the absorbent foam layer, where the second barrier layer has a first side and a second side opposite the first side, and the second side of the second barrier layer is in contact with the first side of the absorbent foam layer; and a third absorbent layer joined to the first side of the second barrier layer.

As used herein, the terms "including," "comprising," or "having" and variations thereof encompass the items listed thereafter and equivalents thereof, as well as additional items. All numerical ranges are inclusive of their endpoints and non-integral values between the endpoints unless otherwise stated. Terms such "top," "bottom," and the like are only used to describe elements as they relate to one another, but are in no way meant to recite specific orientations of an article or apparatus, to indicate or imply necessary or required orientations of an article or apparatus, or to specify how an article or apparatus described herein will be used, mounted, displayed, or positioned in use.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

DETAILED DESCRIPTION

The present invention relates to a method of making absorbent foam composites that comprise an absorbent foam layer and a second absorbent layer. The present invention also relates to absorbent foam composites made therefrom. The absorbent foam composites can be used in a variety of applications, including disposable absorbent articles such as personal hygiene articles, medical bandages, pet pads and agricultural pads.

Figure 1:
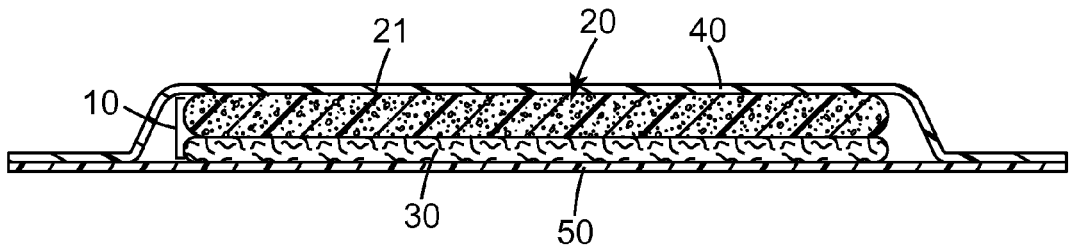
FIG. 1 is a cross-sectional view of an absorbent article.

FIG. 1 illustrates one type of absorbent article disclosed in U.S. Ser. No. 61/652,408 comprising an absorbent foam composite 10 disposed between a fluid pervious topsheet 40 and fluid impervious backsheet 50. The absorbent foam composite comprises a first absorbent layer 20 and a second absorbent layer 30 in fluid communication with each other. The first absorbent layer 20 comprises a polymeric foam 21.

The absorbent foam layer is typically made by well-known casting processes and includes pumping the ingredients used to make the foam to a meter mixing head, dispensing the reaction mixture between a bottom release liner and a top release liner, feeding the mixture and release liners through nip rolls of a predetermined gap to control the spreading and/or the thickness of the foam, curing the foam, and removing the release liners from the cured foam. The absorbent foam layer and second absorbent layer are then joined together. Although this process results in a functional absorbent foam composite, it is not particularly cost effective or efficient. For example, the cost of the throw-away release liners during the foam casting step can exceed 50% of the raw material cost of the foam.

One solution is to replace one or both release liners with the second absorbent layer and cast the foam directly onto the second absorbent layer. However, it was found that the foam reaction mixture would often penetrate the second absorbent layer during the casting process. This was particularly problematic when the second absorbent layer comprised fibrous material, superabsorbent polymer or a combination of the two. For example, foam monomers or prepolymers will penetrate the second absorbent layer and bind at least some of the fibrous material and/or superabsorbent polymer, rendering the second absorbent layer less effective.

The present method overcomes the above problems by placing a barrier layer between the absorbent foam layer and second absorbent layer and breaching the barrier layer once the foam has cured so that fluid can pass from the absorbent foam layer to the second absorbent layer (i.e., the absorbent layers are in fluid communication). Generally, the method comprises casting an absorbent foam layer having a first side and a second side opposite the first side onto a barrier layer having a first side and a second side opposite the first side, where the second side of the absorbent foam layer is in contact with the first side of the barrier layer; joining a second absorbent layer to the second side of the barrier layer before, during, or after the casting step; and breaching the barrier layer after the casting step so that the absorbent foam layer and second absorbent layer are in fluid communication.

Alternatively, the method comprises casting an absorbent foam layer having a first side and a second side opposite the first side onto a barrier layer having a first side and a second side opposite the first side, where the second side of the absorbent foam layer is in contact with the first side of the barrier layer; joining a second absorbent layer to the second side of the barrier layer before, during, or after the casting step; adding a second barrier layer to the first side of the absorbent foam layer during the casting step, where the second barrier layer has a first side and a second side opposite the first side, and the second side of the second barrier layer is in contact with the first side of the absorbent foam layer; joining a third absorbent layer to the first side of the second barrier layer before, during or after the casting step; breaching the two barrier layers so that the absorbent foam layer is in fluid contact with each of the second and third absorbent layers; and skiving the foam layer to create two absorbent foam composites.

The methods of the present invention reduce or eliminate the need for expensive release liners and allow the absorbent foam layer and absorbent foam composite to be prepared on the same production line.

Figure 2:
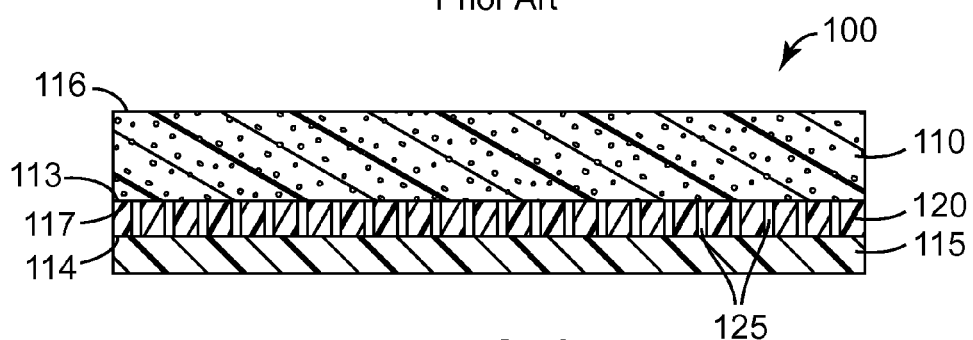
FIG. 2 is a cross-sectional view of an absorbent foam composite produced by the method of the present invention.

An exemplary foam composite made by the method of the present invention is illustrated in FIG. 2. The absorbent foam composite 100 comprises a barrier layer 120 having a first side 113 and a second side 114 opposite the first side 113, and an absorbent foam layer 110 having a first side 116 and a second side 117 opposite the first side 116. The second side 117 of the absorbent foam layer 110 is joined to the first side 113 of the barrier layer 120. A second absorbent layer 115 is joined to the second side 114 of the barrier layer 120. Breaches 125 in the barrier layer 120 permit fluid communication between the absorbent foam layer 110 and second absorbent layer 115.

Both the absorbent foam layer and second absorbent layer will absorb fluids. The actual distribution of fluids between the layers can vary depending upon, for example, the nature of the fluid and composition of the absorbent layers. In a favored embodiment, the absorbent foam layer functions primarily as a distribution layer and the second absorbent layer functions primarily as a storage layer. Upon insult with fluid, the absorbent foam layer will wick (i.e., transport) the fluid in the "x" and "y" direction while also carrying the fluid in the "z" direction to the second absorbent layer. The resultant distribution of fluid between the absorbent foam layer and second absorbent layer can vary. However, to improve re-wet performance, it is preferable that more of the fluid end up in the second absorbent layer than the absorbent foam layer.

Figure 3:
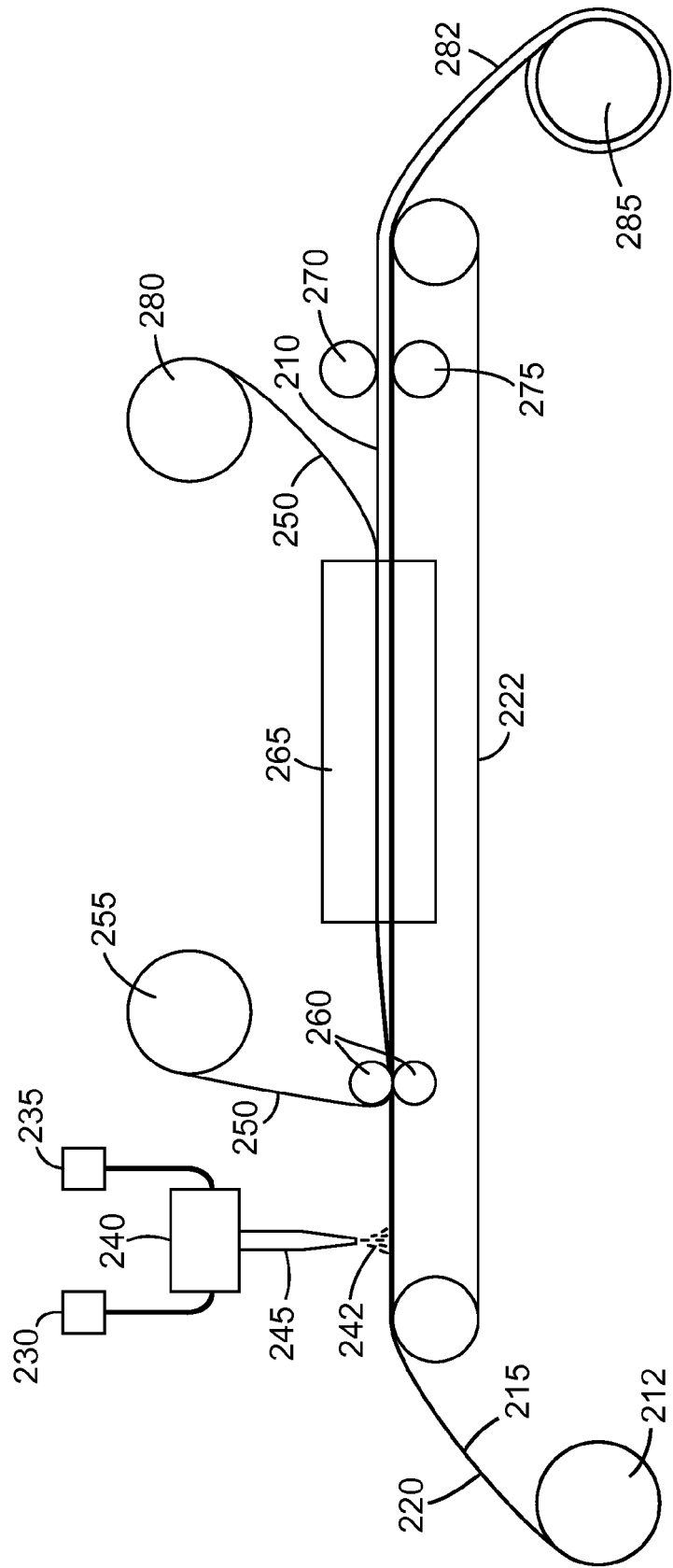
FIG. 3 is a schematic view of an apparatus used to carry out the method of the present invention.

An exemplary method of making the foam composite of FIG. 2 is illustrated in FIG. 3. The barrier layer 220 and second absorbent layer 215 are combined off-site and supplied via supply roll 212. Alternatively (not shown), the barrier layer and second absorbent layer can be supplied via separate supply rolls and laminated together in the production line. The second absorbent layer can be joined to the barrier layer before, during or after the foam casting step. The barrier layer and second absorbent layer can be joined together by any suitable technique. In some embodiments, the layers are adhesively laminated together. Examples of suitable adhesives include emulsion, hot melt, curable, or solvent-based adhesives. Suitable pressure sensitive adhesives include (meth)acrylate-based pressure sensitive adhesives, polyurethane adhesives, natural or synthetic rubber-based adhesives, epoxy adhesives, curable adhesives, phenolic adhesives, and the like. In other embodiments, the barrier layer can be applied to one side of the second absorbent layer by polycoating techniques.

The barrier layer 220 and second absorbent layer 215 are driven in the production line by a conveyor belt 222. Alternatively (not shown), the barrier layer and second absorbent layer may be drawn in a controlled tension environment such that they will move at the same speed as provided by a conveyor belt. The controlled tension environment can be created by a winder which is located at the end of the production line. The winder imparts sufficient tension to unwind the barrier and second absorbent layers from their supply roll(s), move them through the production line, and wind the finished product into a jelly roll configuration on the winder. In yet another alternative, the production line could combine a winder with a conveyor belt.

The foam ingredients are supplied via inlet tubes 230, 235 to a meter mixing head 240. Although only two inlet tubes 230, 235 are shown, it should be understood that additional inlet tubes may be provided as needed. The meter mixing head 240 mixes the foam ingredients and discharges the reaction mixture 242 through nozzle 245 onto the barrier layer 220. The method of and means for depositing the reaction mixture 242 onto the barrier layer 220 is not critical. In some embodiments, the reaction mixture 242 is deposited in a side-to-side configuration, perpendicular to the machine direction.

A release liner 250 is applied to the top side of the reaction mixture 242 via supply roll 255. Then, the release liner 250, the foam reaction mixture 242, the barrier layer 220 and the second absorbent layer 215 are passed through metering rolls 260 having a predetermined gap to evenly distribute the reaction mixture 242 and/or control the thickness of the resultant absorbent foam layer 210. Although only one set of metering rolls 260 are shown, two or more sets of metering rolls are also contemplated. The reaction mixture is then cured in an oven 265. The exact temperature range will depend upon the nature of the foam. In some embodiments, the curing temperature ranges from 100° F. to 275° F. For the purposes of this disclosure, the term "casting step" covers deposition of the reaction mixture onto the barrier layer through curing of the reaction mixture.

After the reaction mixture has cured, the barrier layer 220 is breached to provide fluid communication between the absorbent foam layer 210 and second absorbent layer 215. In FIG. 3, the release liner 250 is removed from the absorbent foam layer 210 by wind roll 280 prior to breaching the barrier layer 220. However, it should be understood that the release liner 250 could be removed later in the production line after the barrier layer 220 has been breached.

There are a number of ways to breach the barrier layer 220. In the particular embodiment shown in FIG. 3, the barrier layer is pin perforated. The absorbent foam layer 210, the barrier layer 220 and the second absorbent layer 215 are passed between a nip created by pin roller 270 and backing roll 275. The pin length and nip gap between the pin roller 270 and backing roll 275 are selected to insure the pins on the pin roller 270 penetrate through at least the barrier layer 220. The pin roller 270 is not limited to any particular pin pattern. The pins could be uniformly or non-uniformly distributed across the roller. A non-uniform distribution would include a roller having regions with pins and regions without pins, whether or not the pins within a region were uniformly distributed or the pattern of regions with or without pins was uniform. In some embodiments, the pins are uniformly distributed across the pin roller and have a density in the range of 20-400 pins/in$^2$. The pins could be of a single gauge or more than one gauge. In some embodiments, the pin gauge ranges from 12 to 28. The exact pattern and gauge will ultimately depend upon the application for which the absorbent foam composite is intended.

As illustrated in FIG. 3, the pins of the pin roller 270 will penetrate through both the foam layer and the barrier layer. It is also possible to have the pins penetrate some, or all, of the second absorbent layer. However, it has been found that in some instances where the second absorbent layer comprises superabsorbent polymer, perforation of the second absorbent layer may result in loss of polymer. In such instances, it is preferable to minimize pin penetration into the second absorbent layer.

Instead of perforating the composite from top down, it is also possible to pin perforate from underneath (i.e. reverse the pin roller 270 and backing roll 275). In such cases, the pins will penetrate both the second absorbent layer and the barrier layer. It is also possible to have the pins penetration some, or all, of the absorbent foam layer. However, in some instances, materials from the second absorbent layer may be pushed by the pins into the foam layer, thus altering one or more properties of the absorbent foam layer.

Although the barrier layer 220 is pin perforated in FIG. 3, other methods for breaching the barrier layer 220 are contemplated. For example, the pin roller 270 could be replaced with a skip slitter. Again, the depth (or length) of the blade and the nip gap between the skip slitter and backing roll are selected to insure the barrier layer is slit. If the skip slitter is above the composite, at least the absorbent foam layer and barrier layer will be slit. If the skip slitter is below the composite, at least the second absorbent layer and barrier layer will be split. As with the pin roller, the skip slitter is not limited to any particular pattern. The number of slits, length of slits, orientation of the slits, and distance between slits will depend upon the application for which the absorbent foam composite is intended. In some embodiments, a 5-2-2 skip slit pattern is used, where the first digit represents the slit length (mm), the second digit represents the distance (mm) between slits in the machine direction, and the third digit represents the distance (mm) between slits in the cross direction and where the adjacent skip slit row is offset by ½ times the repeat length. In addition to a skip slitting, it is contemplated that slitting (and perforation) of the barrier layer could also be accomplished using currently available laser technology.

Once the barrier layer has been perforated in FIG. 3, the absorbent foam composite 282 is wound on a wind up roll 285. Alternatively, the finished article could be fed directly into a process line for making articles comprising the absorbent foam composite.

Although the steps in FIG. 3 are performed on the same manufacturing line, it is contemplated that the perforation step could be performed on a separate manufacturing line prior to, or during, the manufacture of an article into which the intermediate composite is incorporated. In other words, although it may be convenient to perform all steps on the same manufacturing line, it is not necessary. In some embodiments, the foam composite that exits the oven is fed to a wind up roll (with or without the release liner) and provided in roll form as an intermediate composite. The intermediate composite would then be perforated at a later time.

Figure 4:
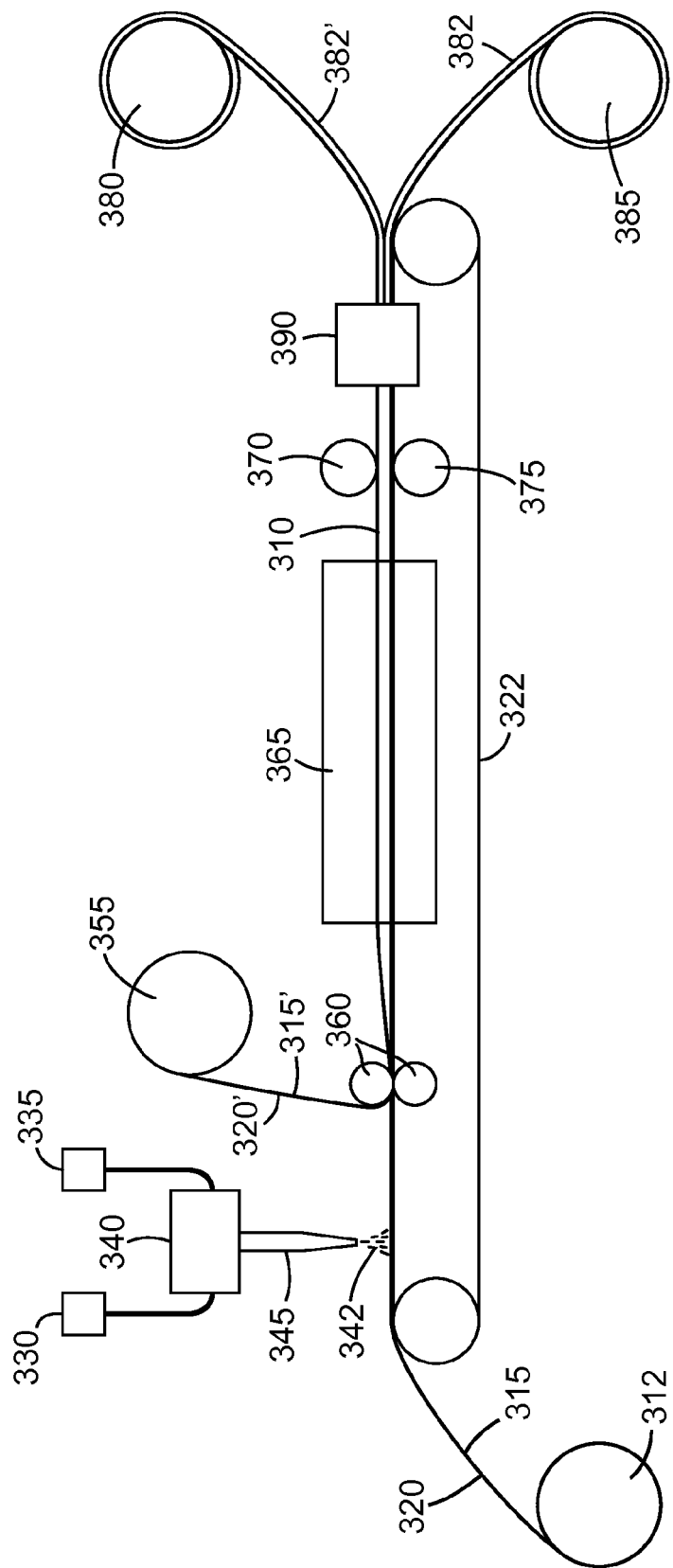
FIG. 4 is a schematic view of an alternative apparatus used to carry out the method of the present invention.

Another exemplary method of the present invention is illustrated in FIG. 4. The method shares many of the same elements and features described above with respect to the method of FIG. 3. Accordingly, elements and features corresponding to elements and features in the illustrated embodiment of FIG. 3 are provided with the same reference numerals in the 300 series. Reference is made to the description above accompanying FIG. 3 for a more complete description of the features and elements (and alternatives to such features and elements) of the embodiment illustrated in FIG. 4.

The method of FIG. 4 differs from the method of FIG. 3 in that the release liner 250 of FIG. 3 is replaced with a second barrier layer 320' and third absorbent layer 315', and the cured foam layer is skived to create two absorbent foam composites. This method completely eliminates release liners from the process, thus reducing material cost and waste.

As illustrated in FIG. 4, the second barrier layer 320' and third absorbent layer 315' are combined off-site and supplied via supply roll 355. Alternatively (not shown), the second barrier layer and third absorbent layer can be supplied via separate supply rolls and laminated together in the production line. The third absorbent layer can be laminated to the second barrier layer before, during or after the foam casting step.

The foam reaction mixture 342, barrier layers 320, 320' and absorbent layers 315, 315' are passed through metering rolls 360 having a predetermined gap to evenly distribute the reaction mixture 342 and/or control the thickness of the resultant absorbent foam layer 310. The reaction mixture is then cured in an oven 365, and the barrier layers 320, 320' are pin perforated by a pin roller 370. The foam layer is then skived using a skiving apparatus 390 to create two absorbent foam composites 382, 382' that are fed to wind up rolls 385, 380, respectively.

Figure 5:
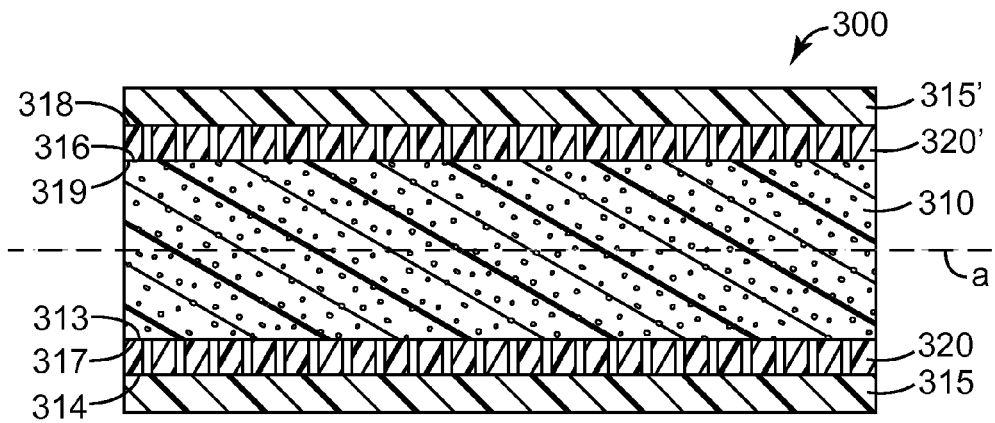
FIG. 5 is a cross-section view of a foam composite before being skived to produce two absorbent foam composites.

The intermediate foam composite created prior to skiving is illustrated in FIG. 5. The composite 300 comprises an absorbent foam layer 310 having a first side 316 and a second side 317 opposite the first side 316, and a barrier layer 320 having a first side 313 and second side 314 opposite the first side 313. The first side 313 of the barrier layer 320 is joined to the second side 317 of the absorbent foam layer 310. A second absorbent layer 315 is joined to the second side 314 of the barrier layer 320. A second barrier layer 320' has a first side 318 and a second side 319 opposite the first side 318. The second side 319 of the second barrier layer 320' is joined to the first side 316 of the absorbent foam layer 310. A third absorbent layer 315' is joined to the first side 318 of the second barrier layer 320'.

Skiving the foam layer along line "a" creates two absorbent foam composites having the configuration shown in FIG. 2. The composites comprise an absorbent foam layer having ½ the thickness of the originally cured foam layer, a barrier layer, and a second (or third) absorbent layer. Although the composite in FIG. 5 could produce two exactly equivalent absorbent foam composites, it should be understood that the barrier layers 320, 320' may be the same or different materials. Similarly, the absorbent layers 315, 315' may be the same or different materials. Additionally, the foam layer may be skived down the center to create two absorbent foam layers of equal thickness, as provided in FIG. 5, or skived off-center to create two foam layers of different thickness.

Although the steps in FIG. 4 are performed on the same manufacturing line, it is contemplated that the perforation and/or skiving steps could be performed elsewhere. In other words, although it may be convenient to perform all steps on the same manufacturing line, it is not necessary. In some embodiments, the foam composite that exits the oven is fed to a wind up roll and provided in roll form as an intermediate composite. The intermediate composite would then be perforated and skived at a later time. In other embodiments, the foam composite is perforated before being fed to a wind up roll and provided in roll form as an intermediate composite. The intermediate composite would then be skived at a later time.

The materials used to make the absorbent foam composites will be described further below.

Absorbent Foam Layer

The absorbent foam layers of the present invention are made with polymeric foams that are predominantly open-celled. Open-celled foams contain individual cells defined by a plurality of mutually connected, three-dimensionally branched webs. The strands of polymeric material making up these branched webs are often referred to as "struts." The cells in such open-celled foam structures have intercellular openings or "windows" that are large enough to permit fluid transfer from one cell to the other within the foam structure. A foam material is typically "open-celled" if at least 80% of the cells in the foam structure that are at least 1 micrometer in size are in fluid communication with at least one adjacent cell. Thus, a portion of the cells (up to 20%) of the foam may be closed.

The polymeric foams used in the present invention are also sufficiently hydrophilic to permit the foam to absorb aqueous fluids. The foam structures can be rendered hydrophilic by the selection of (e.g. hydrophilic) components during the formation of the polymeric foam or by post-treatment.

Exemplary polymers suitable in implementation of the present invention include polymers selected from the group consisting of polyurethanes, polyacrylics, and melamine-formaldehyde polymers. By way of example, some suitable polyurethanes will be described in further detail below.

Polyurethane foams can be made by mixing together polyisocyanates, polyols, water (and/or a chemical blowing agent) and optional additives, allowing the mixture to foam, and curing the foamed mixture. In practice, it is common to provide the polyisocyanate(s) in one liquid stream and a blend of the polyol(s), water (and/or chemical blowing agent) and optional additives in a second liquid stream. The streams are often referred to as "iso" and "poly", respectively, and when combined produce the polyurethane foam. More than two liquid streams may be contemplated. However, the polyisocyanates and blend of polyols and water (and/or chemical blowing agent) are kept in separate liquid streams.

The polyisocyanate component may comprise one or more polyisocyanates. Various aliphatic and aromatic polyisocyanates have been described in the art. The polyisocyanates utilized in forming the polyurethane foam typically have a functionality between 2 and 3.

In one embodiment, the foam is prepared from at least one aromatic polyisocyanate. Examples of aromatic polyisocyanates include toluene 2,4- and 2,6-diisocyanate (TDI), naphthalene 1,5-diisocyanate, and 4,4'-, 2,4'- and 2,2'-methylene diphenyl diisocyanate (MDI).

In favored embodiments, the foam is prepared from one or more (e.g. aromatic) polymeric polyisocyanates. Polymeric polyisocyanates typically have a (weight average)

molecular weight greater than a monomeric polyisocyanate (lacking repeating units), yet lower than a polyurethane prepolymer. The linking groups in polymeric polyisocyanates may include isocyanurate groups, biuret groups, carbodiimide groups, uretonimine groups, uretdione groups, etc. as known in the art.

Some polymeric polyisocyanates may be referred to as "modified monomeric isocyanate". For example, pure 4,4'-MDI is a solid having a melting point of 38° C. and an equivalent weight of 125 g/equivalent. However, modified MDIs are liquid at 38° C. and have a higher equivalent weight (e.g. 143 g/equivalent). The difference in melting point and equivalent weight is believed to be a result of a small degree of polymerization, such as by the inclusion of linking groups, as described above.

Polymeric polyisocyanates, including modified monomeric polyisocyanates, may comprise a mixture of monomer in combination with polymeric species inclusive of oligomeric species. For example, polymeric MDI is reported to contain 25-80% monomeric 4,4'-methylene diphenyl diisocyanate as well as oligomers containing 3-6 rings and other minor isomers, such as 2,2' isomer.

In some embodiments, the polymeric polyisocyanates have a viscosity from about 10 to 300 cps at 25° C., an equivalent weight from about 130 to 250 g/equivalent, and an average molecular weight (Mw) of no greater than about 500 Da.

In some embodiments, the polyurethane is derived from a single polymeric polyisocyanate or a blend of polymeric isocyanates. Thus, 100% of the polyisocyanate component is polymeric polyisocyanate(s). In other embodiments, a major portion of the polyisocyanate component is a single polymeric polyisocyanate or a blend of polymeric isocyanates. In these embodiments, at least 50, 60, 70, 75, 80, 85 or 90 wt-% of the polyisocyanate component is polymeric isocyanate(s).

Commercially available polyisocyanates include SUPRASEC® 9561 from Huntsman Chemical Company in The Woodlands, Tex.

The aforementioned isocyanates are reacted with a polyol to prepare the polyurethane foam material. The polyurethane foams are hydrophilic, such that the foam absorbs aqueous liquids, particularly body fluids. The hydrophilicity of the polyurethane foams is typically provided by use of an isocyanate-reactive component, such as a polyether polyol, having a high ethylene oxide content. Examples of suitable polyols include adducts [e.g., polyethylene oxide, polypropylene oxide, and poly(ethylene oxide-propylene oxide) copolymer] of dihydric or trihydric alcohols (e.g., ethylene glycol, propylene glycol, glycerol, hexanetriol, and triethanolamine) and alkylene oxides (e.g., ethylene oxide, propylene oxide, and butylene oxide). Polyols having a high ethylene oxide content can also be made by other techniques as known in the art. Suitable polyols typically have a molecular weight (Mw) of 100 to 5,000 Da and contain an average functionality of 2 to 3.

The polyurethane foam is typically derived from (or in other words is the reaction product of) at least one polyether polyol having ethylene oxide (e.g. repeat) units. The polyether polyol typically has an ethylene oxide content of at least 10, 15, 20 or 25 wt-% and typically no greater than 75 wt-%. Such polyether polyol has a higher functionality than the polyisocyanate. In some embodiments, the average functionality is about 3. The polyether polyol typically has a viscosity of no greater than 1000 cps at 25° C. and in some embodiments no greater than 900, 800, or 700 cps. The molecular weight of the polyether polyol is typically at least 500 or 1000 Da and in some embodiments no greater than 4000 or 3500, or 3000 Da. Such polyether polyol typically has a hydroxyl number of at least 125, 130, or 140. Commercially available polyols include the polyether polyols CDB-33142 and CARPOL® GP-5171 from Carpenter Company in Richmond, Va.

In some embodiments, one or more polyether polyols having a high ethylene oxide content and a molecular weight (Mw) of no greater than 5500, or 5000, or 4500, or 4000, or 3500, or 3000 Da, as just described, are the primary or sole polyether polyols of the polyurethane foam. For example, such polyether polyols constitute at least 50, 60, 70, 80, 90, 95 or 100 wt-% of the total polyol component. Thus, the polyurethane foam may comprise at least 25, 30, 35, 40, 45 or 50 wt-% of polymerized units derived from such polyether polyols.

In other embodiments, one or more polyether polyols having a high ethylene oxide content are utilized in combination with other polyols. In some embodiments, the other polyols constitute at least 1, 2, 3, 4, or 5 wt-% of the total polyol component. The concentration of such other polyols typically does not exceed 40, or 35, or 30, or 25, or 20, or 15, or 10 wt-% of the total polyol component, i.e. does not exceed 20 wt-%, or 17.5 wt-%, or 15 wt-%, or 12.5 wt-%, or 10 wt-%, or 7.5 wt-%, or 5 wt-% of the polyurethane reaction mixture. Commercially available polyols include CARPOL® GP-700 from Carpenter Company in Richmond, Va. and ARCOL® E-434 from Bayer Material Science, Pittsburgh, Pa. In some embodiments, such optional other polyols may comprise polypropylene (e.g. repeat) units.

The polyurethane foam generally has an ethylene oxide content of at least 10, 11, or 12 wt-% and no greater than 20, 19, or 18 wt-%.

The kinds and amounts of polyisocyanate and polyol components are selected such that the polyurethane foam is relatively soft, yet resilient. In the production of polyurethane foams, the polyisocyanate component and polyol component are reacted such that an equivalence ratio of isocyanate groups to the sum of hydroxyl groups is no greater than 1 to 1. In some embodiments, the components are reacted such that there are excess hydroxyl groups (e.g. excess polyol). In such embodiments, the equivalence ratio of isocyanate groups to the sum of the hydroxy groups is at least 0.7 to 1.

The polyurethane is foamed by mixing the reactants in liquid form with a suitable amount of water or chemical blowing agent, suitable catalyst and other optional components, and allowing the mixture to foam and cure. It is preferred to use water for producing the polyurethane foams, because the water reacts with the isocyanate groups to liberate carbon dioxide. The amount of water is preferably in the range from 0.5 to 5 wt-% of the polyurethane reaction mixture. In some embodiments, the amount of water is no greater than 4 or 3 or 2 or 1 wt-% of the polyurethane reaction mixture.

The polyurethane typically comprises a surfactant to stabilize the foam. Various surfactants have been described in the art. In one embodiment, a silicone surfactant is employed that comprises ethylene oxide (e.g. repeat) units, optionally in combination with propylene oxide (e.g. repeat) units such DABCO® DC-198 from Air Products in Allentown, Pa. In some embodiments, the concentration of hydrophilic surfactant typically ranges from about 0.05 to 1 or 2 wt-% of the polyurethane reaction mixture.

The polyurethane foam may optionally comprise known and customary polyurethane formation catalysts such as organic tin compounds and/or an amine-type catalyst. The catalysts are preferably used in an amount of from 0.01 to 5 wt-% of the polyurethane reaction mixture. The amine-type catalyst is typically a tertiary amine. Examples of suitable tertiary amines include monoamines such as triethylamine, and dimethyl cyclohexylamine; diamines such as tetramethylethylenediamine, and tetramethylhexanediamine; triamines such as tetramethylguanidine; cyclic amines such as triethylenediamine, dimethylpiperadine, and methylmorphorine; alcoholamines such as dimethylaminoethanol, trimethylaminoethylethanolamine, and hydroxyethylmorphorine; ether amines such as bisdimethylaminoethyl ethanol; diazabicycloalkenes such as 1,5-diazabicyclo(5,4,0)undecene-7 (DBU), and 1,5-diazabicyclo(4,3,0)nonene-5; and organic acid salts of the diazabicycloalkenes such as phenol salt, 2-ethylhexanoate and formate of DBU. These amines can be used either singly or in combination. The amine-type catalyst can be used in an amount no greater than 4, 3, 2, 1 or 0.5 wt-% of the polyurethane. Commercially available catalysts include DABCO® BL-17 and DABCO® 33-LV from Air Products Company in Allentown, Pa.

The polyurethane foam may optionally comprise a superabsorbent polymer (SAP), also referred to as "hydrogels" and "hydrocolloids". The SAP is substantially water-insoluble but consists of water-swellable polymers capable of absorbing large quantities of liquids (e.g. 10-100 times their weight). Various SAP materials have been described in the art (see, e.g., U.S. Pat. No. 4,410,571; U.S. Pat. No. 6,271,277; and U.S. Pat. No. 6,570,057). Suitable SAP materials include superabsorbents with low gel strength, high gel strength, surface cross-linked superabsorbents, uniformly cross-linked superabsorbents, or superabsorbents with varied cross-link density throughout the structure. Superabsorbents may be based on chemistries that include poly(acrylic acid), poly(iso-butylene-co-maleic anhydride), poly(ethylene oxide), carboxy-methyl cellulose, poly(-vinyl pyrrolidone), and poly(-vinyl alcohol). The superabsorbents may range in swelling rate from slow to fast. The superabsorbents may be in various degrees of neutralization. Counter-ions are typically $Li^+$, $Na^+$, and $K^+$. Commercially available SAP includes LiquiBlock™ HS Fines from Emerging Technologies Inc. in Greensboro, N.C.

Favored SAP materials can be slightly network cross-linked polymers of partially neutralized polyacrylic acids or starch derivatives thereof. For example, the SAP may comprise from about 50 to about 95%, preferably about 75%, neutralized, slightly network crosslinked, polyacrylic acid (i.e. poly(sodium acrylate/acrylic acid)). As described in the art, network crosslinking serves to render the polymer substantially water-insoluble and, in part, determines the absorptive capacity and extractable polymer content characteristics of the precursor particles and the resultant macrostructures.

For embodiments wherein the polyurethane foam comprises SAP, the SAP is generally present within the foam as discrete pieces. Such pieces may have various shapes such as spherical, rounded, angular, or irregular pieces as well as fibers. The particles generally comprise a distribution of sizes ranging from about 1 micron to 500 microns in diameter or cross-section (largest dimension when not spherical). The particles are preferably a finely divided powder of a maximum particle size of less than 400, 300, or 200 microns.

When present, the concentration of SAP in the polyurethane foam is typically at least 1, 2, 3, 4, or 5 wt-% of the polyurethane reaction mixture and typically no greater than 30, 25, or 20 wt-% of the polyurethane reaction mixture. The minimal amount of SAP that can provide the desired properties (e.g. absorption capability, strike-through, rewet) is utilized. In some embodiments, the concentration of SAP is no greater than 17.5, or 15, or 12.5 or 10 wt-% of the polyurethane reaction mixture. In some embodiments, the inclusion of the SAP in the foam has little or no affect on the absorption capacity of the foam, yet surprisingly improves the strike-through and rewet of the foam and especially the absorbent foam composite.

The polyurethane foams may also optionally comprise pigments. It is common practice in the personal hygiene industry to print graphics, color and/or color indicators onto one or more layers of a hygiene article. Printing can be complicated and expensive. By coloring the absorbent foam layer, personal hygiene manufactures can incorporate color into their products without the need for specialized printing equipment and inks. In preferred embodiments, the pigment comes in a polyol carrier and is added to the poly liquid stream during manufacture of the polyurethane foam. Commercially available pigments include DispersiTech™ 2226 White, DispersiTech™ 2401 Violet, DispersiTech™ 2425 Blue, DispersiTech™ 2660 Yellow, and DispersiTech™ 28000 Red from Milliken in Spartansburg, S.C. and Pdi® 34-68020 Orange from Ferro in Cleveland, Ohio.

The polyurethane foam may optionally comprise other additives such as surface active substances, foam stabilizers, cell regulators, blocking agents to delay catalytic reactions, fire retardants, chain extenders, cross-linking agents, external and internal mold release agents, fillers, colorants, optical brighteners, antioxidants, stabilizers, hydrolysis inhibitors, as well as anti-fungal and anti-bacteria substances. Such other additives are typically collectively utilized at concentrations ranging from 0.05 to 10 wt-% of the polyurethane reaction mixture. Commercially available additives include DABCO®BA-100 (polymeric acid blocking agent) from Air Products Company in Allentown, Pa. and Triethanolamine LFG (cross-linking agent) from Dow Chemical Company in Midland, Mich.

The polyurethane foam typically has an average basis weight of at least 100, 150, 200, or 250 gsm and typically no greater than 500 gsm. In some embodiments the average basis weight is no greater than 450, or 400 gsm. The average density of the polyurethane foam is typically at least 3, 3.5 or 4 lbs/ft$^3$ and no greater than 7 lbs/ft$^3$.

The above description provides one technique for making suitable polyurethane foams. One can contemplate other techniques as well. For example, another technique for making suitable polyurethane foams is known as the "prepolymer" technique. In this technique, a prepolymer of polyol and isocyanate are reacted in an inert atmosphere to form a liquid polymer terminated with isocyanate groups. To produce the foamed polyurethane, the isocyanate-terminated prepolymer is thoroughly mixed with water and, optionally, a polyol in the presence of a catalyst or a cross-linker.

Release Liners

In some embodiments of the present invention, a release liner is applied to one side of the foam reaction mixture during the casting step. Any conventional release liner may be used. Exemplary release liners include olefins (e.g., polyethylene and polypropylene) and coated papers. Silicone coated papers are less preferred since the silicone has a tendency to transfer to the surface of the foam layer, thus rendering the surface less hydrophilic. Commercially available release liners include 19PP/12PTC1/19PP PERF from Prolamina in Neenah, Wis. and MUL/BC 58 from Schoeller Company in Polaski, N.Y.

Barrier Layer

Suitable barrier layers prevent the foam reaction ingredients from penetrating the second (or third) absorbent layer during the casting step. The barrier layer must have the capability of being breached after the foam has cured so that fluid can transfer from the absorbent foam layer to the second (or third) absorbent layer during use. The barrier layer can be breached by any number of methods, including perforation (e.g., pin perforation), slitting (e.g., skip slitting) or decomposition. The barrier layer should not affect the softness, drape or flexibility of the absorbent foam composite, and the barrier layer must be thermally stable at foam curing temperatures (typically 100° F.-275° F.). Barrier layers can include films, coated nonwoven materials, and coated papers. Exemplary barrier films include polyolefin films (e.g., polypropylene, polyethylene, and co-polymers thereof) and polyester films. Exemplary coatings for nonwoven materials and papers include fluoropolymer and polysilicone.

Second Absorbent Layer

The second absorbent layer may comprise a variety of liquid-absorbent materials. Exemplary absorbent materials include natural and synthetic fibers, absorbent foams, absorbent sponges, superabsorbent polymers, absorbent gelling materials, or any equivalent material or combinations of materials, or mixtures of these.

The fibers of the second absorbent layer are hydrophilic, or a combination of both hydrophilic and hydrophobic fibers. Suitable fibers include those that are naturally occurring fibers (modified or unmodified), as well as synthetically made fibers. Examples of suitable unmodified/modified naturally occurring fibers include cotton, Esparto grass, bagasse, hemp, flax, silk, wool, wood pulp, chemically modified wood pulp, jute, rayon, ethyl cellulose, and cellulose acetate.

Suitable wood pulp fibers can be obtained from known chemical processes such as, but not limited to the Kraft and sulfite processes. A further suitable type of fibers is chemically stiffened cellulose, i.e., stiffened by chemical means to increase the stiffness of the fibers under both dry and aqueous conditions. Such means can include the addition of a chemical stiffening agent that, for example, coats and/or impregnates the fibers or by stiffening of the fibers by altering the chemical structure, e.g., by crosslinking polymer chains, as known in the art. Curl may be imparted to the fibers by methods including chemical treatment or mechanical twisting. Curl is typically imparted before crosslinking or stiffening.

Hydrophilic fibers, particularly (optionally modified) cellulosic fibers are typically preferred. However, hydrophilic fibers can also be obtained by hydrophilizing hydrophobic fibers, such as surfactant-treated or silica-treated thermoplastic fibers. Surfactant-treated fibers can be made by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber.

Suitable synthetic fibers can be made from polyvinyl chloride, polyvinyl fluoride, polytetrafluoroethylene, polyvinylidene chloride, polyacrylics, polyvinyl acetate, polyethylvinyl acetate, non-soluble or soluble polyvinyl alcohol, polyolefins such as polyethylene and polypropylene, polyamides such as nylon, polyesters, polyurethanes, polystyrenes, and the like. In some embodiments, the synthetic fibers are thermoplastic, e.g. having a melt point of at least 50° C.-75° C. and no greater than 190 or 175° C.

Generally the (e.g. thermoplastic) synthetic fibers have an average width, diameter, or cross-section dimension of at least 5, 10, 15, or 20 microns. The average diameter may range up to 1000 microns (1 mm), yet is typically no greater than 800 microns, or 700 microns, or 600 microns, and in some embodiments no greater than 500 microns or 400 microns. In some embodiments, the average diameter of the fibers of the web is no greater than 300, 250, 200, 150, 100, 75 or 50 microns. Smaller diameter staple fiber webs can provide improved flexibility (e.g. a lower work of compression). The filament cross sectional dimension (and shape of the cross section) is preferably substantially, or essentially, uniform along the length of the filament, e.g., uniformly round. The surface of the filament is typically smooth. The fibers can be in the shape or form of fibers, strips, or other narrow and long shapes. Aggregations can be made up of a plurality of fibers with the same or different plastic compositions, geometric shapes, sizes, and/or diameters. The fibers are typically solid. The fibers can be circular or round in cross section or non-circular in cross section, e.g., lobal, elliptical, rectangular, triangular, and shapes with radial arms such as "x-shaped". For embodiments wherein a thermoplastic fiber is formed from melt-extrusion processes (e.g. spunbond or melt blown) the length of the fibers is continuous. The length of the staple fibers (i.e. fibers) is typically at least 1, 2, or 3 cm, and commonly no greater than 15 cm. In some embodiments, the length of the fibers is no greater than 10, 9, 8, or 7 cm.

The second absorbent layer may be a preformed fibrous web. There are a variety of "dry-laid" and "wet-laid" webmaking processes described in the art. Various absorbent layers and methods of making such have been described in the art. See, for example, U.S. Pat. No. 4,610,678 and U.S. Pat. No. 6,896,669.

The configuration and construction of the second absorbent layer may be varied (e.g., the second absorbent layer may have varying caliper zones (e.g., profiled so as to be thicker in the center), hydrophilic gradients, superabsorbent gradients, or lower density and lower average basis weight acquisition zones). The total absorbent capacity of the second absorbent layer should, however, be compatible with the design loading and the intended use of the absorbent foam composite. In preferred embodiments, the absorption capacity of the second absorbent layer is greater than that of the absorbent foam layer. In some embodiments, the absorption capacity of the second absorbent layer is 1.5×, 2×, 2.5× or even 3× that of the absorbent foam layer.

In some embodiments, the second absorbent layer comprises superabsorbent polymer sandwiched between two layers of cellulosic fiber tissue. Commercially available products having a similar construction include Gelok 5240-72 from Gelok International in Dunbridge, Ohio.

In other embodiments, the second absorbent layer comprises a preformed fibrous web with superabsorbent polymer dispersed within. In particular embodiments, the fibers are a cellulosic fibers.

In yet other embodiments, the second absorbent layer comprises a layer of superabsorbent polymer and a tissue layer (e.g., cellulosic fiber). The superabsorbent polymer layer will face the barrier layer in the final construction of the absorbent foam composite.

In yet another embodiment, the second absorbent layer has a basis weight from about 100 g/m² to about 700 g/m² which has been air-laid as a bottom layer of wood pulp fibers, a middle layer of wood pulp fibers and superabsorbent polymer disposed in amongst the fibers, and a top layer containing at least some wood pulp fibers.

The second absorbent layer is joined to the barrier layer before, during, or after the foam casting step in the method of the present invention. The barrier layer and second absorbent layer can be joined by any suitable technique. In some embodiments, the layers are adhesively laminated together. Examples of suitable adhesives include emulsion, hot melt, curable, or solvent-based adhesives. Suitable pressure sensitive adhesives include (meth)acrylate-based pressure sensitive adhesives, polyurethane adhesives, natural or synthetic rubber-based adhesives, epoxy adhesives, curable adhesives, phenolic adhesives, and the like. In other embodiments, the barrier layer can be applied to one side of the second absorbent layer by polycoating techniques.

It should be understood that the above description also applies to the third absorbent layer described with respect to FIGS. 4 and 5.

Absorbent Foam Composite

A variety of permutations are possible for the construction of the absorbent foam composite based upon the choice of materials for the foam layer, barrier layer, and second absorbent layer. For example, in some embodiments, the absorbent foam composite comprises a polyurethane foam layer, a perforated polyester film barrier layer, and a second absorbent layer comprising superabsorbent polymer sandwiched between two layers of cellulosic fiber tissue. In yet other embodiments, the polyurethane foam layer contains superabsorbent polymer.

Irrespective of the construction, the absorbent foam layer and second absorbent layer can be processed into various shapes including symmetrical (having a point, line, or plane of symmetry) or unsymmetrical shapes. Shapes that are envisioned include but are not limited to circles, ovals, squares, rectangles, pentagons, hexagons, octagons, trapezoids, truncated pyramids, hourglasses, dumbbells, dog bones, etc. The edges and corners can be straight or rounded. In some embodiments, the absorbent foam composite has an hour-glass or trapezoid shape.

It is also contemplated that the absorbent foam layer can be further processed to contain cut-out regions that create voids, cavities, depressions, channels, or grooves. In addition, features may be added to the surface of the absorbent foam layer by a variety of embossing techniques. For example, in the method of FIG. 3, a structured release liner could be used to add structure to the surface of the absorbent foam layer. Alternatively, structure could be added to the absorbent foam composite of FIG. 2 by embossing the absorbent foam layer with a heated plate having the desired pattern. In yet another alternative, the skiving apparatus in FIG. 4 could be designed to impart structure to the surface of the absorbent foam layer during skiving.

Applications

The absorbent foam composites can be used in a variety of applications, including disposable absorbent articles such as personal hygiene articles (e.g., infant diapers, feminine hygiene pads and adult incontinence devices), medical bandages, pet pads and agricultural pads.

Figure 6:
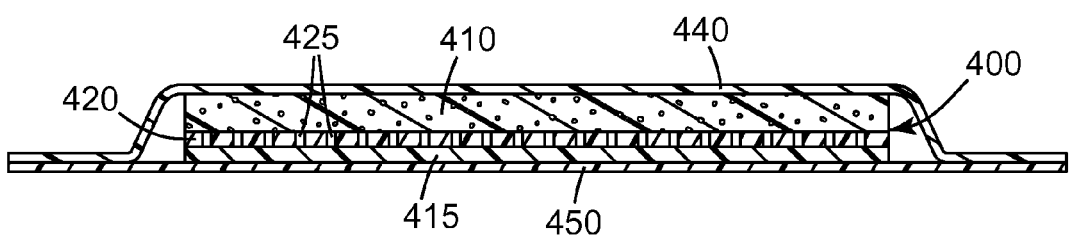
FIG. 6 is a cross-section view of an absorbent article comprising an absorbent foam composite produced by a method of the present invention.

FIG. 6 depicts a cross-sectional view of an absorbent article comprising an absorbent foam composite made by the method of the present invention. The absorbent article comprises a liquid permeable topsheet 440, a liquid impermeable backsheet 450 and an absorbent foam composite 400 therebetween.

The liquid permeable topsheet 440 can consist of a nonwoven layer, porous foams, apertured plastic films, etc. Materials suitable for a topsheet should be soft and non-irritating to the skin and be readily penetrated by fluids. In some embodiments, the top sheet is less hydrophilic than the absorbent foam layer. In some preferred embodiments, the top sheet is made from a hydrophobic material. Exemplary hydrophobic materials include spun bond nonwovens comprising ethylene polymers, polypropylene polymers, and/or copolymers thereof.

The liquid impermeable backsheet 450 may consist of a thin plastic film, e.g., a polyethylene or polypropylene film, a nonwoven material coated with a liquid impervious material, a hydrophobic nonwoven material which resists liquid penetration, or laminates of plastic films and nonwoven materials. The backsheet material may be breathable so as to allow vapour to escape from the absorbent foam composite 400, while still preventing liquids from passing through the backsheet material.

The absorbent foam composite 400 comprises an absorbent foam layer 410, a second absorbent layer 415, and a barrier layer 420 in-between the two absorbent layers 410, 415. Breaches 425 in the barrier layer 420 permit fluid communication between the two absorbent layers 410, 415.

The topsheet 440 and the backsheet 450 typically extend beyond the absorbent foam composite 400 and are connected to each other, e.g., by gluing or welding by heat or ultrasonic, about the periphery of the absorbent foam composite 400. The topsheet 440 and/or the backsheet 450 may further, or alternatively, be attached to the absorbent foam core by any method known in the art, such as adhesive, heatbonding etc.

Some Embodiments of the Disclosure

In a first embodiment, the present disclosure provides a method of making an absorbent foam composite comprising casting an absorbent foam layer having a first side and a second side opposite the first side onto a barrier layer having a first side and a second side opposite the first side, where the second side of the absorbent foam layer is in contact with the first side of the barrier layer; joining a second absorbent layer to the second side of the barrier layer before, during, or after the casting step; and breaching the barrier layer after the casting step so that the absorbent foam layer and second absorbent layer are in fluid communication.

In a second embodiment, the present disclosure provides the method of the first embodiment, wherein the absorbent foam layer comprises polyurethane foam.

In a third embodiment, the present disclosure provides the method of the second embodiment, wherein the polyurethane foam comprises superabsorbent polymer.

In a fourth embodiment, the present disclosure provides the method of any one of the first to third embodiments, wherein the second absorbent layer comprises superabsorbent polymer sandwiched between two layers of cellulosic fiber tissue.

In a fifth embodiment, the present disclosure provides the method of any one of the first to third embodiments, wherein the second absorbent layer comprises a preformed fibrous web with superabsorbent polymer dispersed within.

In a sixth embodiment, the present disclosure provides the method of any one of the first to third embodiments, wherein the second absorbent layer comprises a layer of superabsorbent polymer and a tissue layer, and the superabsorbent polymer layer is sandwiched between the barrier layer and the tissue layer.

In a seventh embodiment, the present disclosure provides the method of any one of the first to sixth embodiments, wherein the barrier layer comprises at least one of films, coated nonwoven materials, and coated papers.

In an eighth embodiment, the present disclosure provides the method of any one of the first to seventh embodiments, wherein the barrier layer comprises polyester film.

In a ninth embodiment, the present disclosure provides the method of any one of the first to seventh embodiments, wherein the barrier layer is a film comprising at least one of polypropylene, polyethylene, and co-polymers thereof.

In a tenth embodiment, the present disclosure provides the method of any one of the first to ninth embodiments, wherein the barrier layer is breached by pin perforation.

In an eleventh embodiment, the present disclosure provides the method of any one of the first to ninth embodiments, wherein the barrier layer is breached by skip slitting.

In a twelfth embodiment, the present disclosure provides the method of any one of the first to eleventh embodiments, wherein the casting step further comprises adding a release layer to the first side of the absorbent foam layer.

In a thirteenth embodiment, the present disclosure provides a method of making an absorbent foam composite comprising taking an intermediate composite comprising a barrier layer having a first side and a second side opposite the first side, an absorbent foam layer joined to the first side of the barrier layer, and a second absorbent layer joined to the second side of the barrier layer; and breaching the barrier layer so that the absorbent foam layer and second absorbent layer are in fluid communication.

In a fourteenth embodiment, the present disclosure provides the method of the thirteenth embodiment, wherein the absorbent foam layer comprises polyurethane foam.

In a fifteenth embodiment, the present disclosure provides the method of the fourteenth embodiment, wherein the polyurethane foam comprises superabsorbent polymer. In a sixteenth embodiment, the present disclosure provides the method of any one of the thirteenth to fifteenth embodiments, wherein the second absorbent layer comprises superabsorbent polymer sandwiched between two layers of cellulosic fiber tissue.

In a seventeenth embodiment, the present disclosure provides the method of any one of the thirteenth to fifteenth embodiments, wherein the second absorbent layer comprises a preformed fibrous web with superabsorbent polymer dispersed within.

In an eighteenth embodiment, the present disclosure provides the method of any one of the thirteenth to fifteenth embodiments, wherein the second absorbent layer comprises a layer of superabsorbent polymer and a tissue layer, and the superabsorbent polymer layer is sandwiched between the barrier layer and the tissue layer.

In a nineteenth embodiment, the present disclosure provides the method of any one of the thirteenth to eighteenth embodiments, wherein the barrier layer comprises at least one of films, coated nonwoven materials, and coated papers.

In a twentieth embodiment, the present disclosure provides the method of any one of the thirteenth to nineteenth embodiments, wherein the barrier layer comprises polyester film.

In a twenty-first embodiment, the present disclosure provides the method of any one of the thirteenth to nineteenth embodiments, wherein the barrier layer is a film comprising at least one of polypropylene, polyethylene, and co-polymers thereof.

In a twenty-second embodiment, the present disclosure provides the method of any one of the thirteenth to twenty-first embodiments, wherein the barrier layer is breached by pin perforation.

In a twenty-third embodiment, the present disclosure provides the method of any one of the thirteenth to twenty-first embodiments, wherein the barrier layer is breached by skip slitting.

In a twenty-fourth embodiment, the present disclosure provides an absorbent foam composite comprising a barrier layer having a first side and a second side opposite the first side; an absorbent foam layer joined to the first side of the barrier layer; and a second absorbent layer joined to the second side of the barrier layer, where the barrier layer has been breached so that the absorbent foam layer and second absorbent layer are in fluid communication.

In a twenty-fifth embodiment, the present disclosure provides the composite of the twenty-fourth embodiment, wherein the absorbent foam layer comprises polyurethane foam.

In a twenty-sixth embodiment, the present disclosure provides the composite of the twenty-fifth embodiment, wherein the polyurethane foam comprises superabsorbent polymer.

In a twenty-seventh embodiment, the present disclosure provides the composite of any one of the twenty-fourth to twenty-sixth embodiments, wherein the second absorbent layer comprises superabsorbent polymer sandwiched between two layers of cellulosic fiber tissue.

In a twenty-eighth embodiment, the present disclosure provides the composite of any one of the twenty-fourth to twenty-sixth embodiments, wherein the second absorbent layer comprises a preformed fibrous web with superabsorbent polymer dispersed within.

In a twenty-ninth embodiment, the present disclosure provides the composite of any one of the twenty-fourth to twenty-sixth embodiments, wherein the second absorbent layer comprises a layer of superabsorbent polymer and a tissue layer, and the superabsorbent polymer layer is sandwiched between the barrier layer and the tissue layer.

In a thirtieth embodiment, the present disclosure provides the composite of any one of the twenty-fourth to twenty-ninth embodiments, wherein the barrier layer comprises at least one of films, coated nonwoven materials, and coated papers.

In a thirty-first embodiment, the present disclosure provides the composite of any one of the twenty-fourth to thirtieth embodiments, wherein the barrier layer comprises polyester film.

In a thirty-second embodiment, the present disclosure provides the composite of any one of the twenty-fourth to thirtieth embodiments, wherein the barrier layer is a film comprising at least one of polypropylene, polyethylene, and co-polymers thereof.

In a thirty-third embodiment, the present disclosure provides a disposable absorbent article comprising the composites of any one of the twenty-fourth to thirty-second embodiments.

In a thirty-fourth embodiment, the present disclosure provides a method of making an absorbent foam composite comprising casting an absorbent foam layer having a first side and a second side opposite the first side onto a barrier layer having a first side and a second side opposite the first side, where the second side of the absorbent foam layer is in contact with the first side of the barrier layer; joining a second absorbent layer to the second side of the barrier layer before, during, or after the casting step; adding a second barrier layer to the first side of the absorbent foam layer during the casting step, where the second barrier layer has a first side and a second side opposite the first side, and the second side of the second barrier layer is in contact with the first side of the absorbent foam layer; joining a third absorbent layer to the first side of the second barrier layer before, during or after the casting step; breaching the two barrier layers so that the absorbent foam layer is in fluid contact with each of the second and third absorbent layers; and skiving the foam layer to create two absorbent foam composites.

In a thirty-fifth embodiment, the present disclosure provides the method of the thirty-fourth embodiment, wherein the two barrier layers are the same materials.

In a thirty-sixth embodiment, the present disclosure provides the method of any one of the thirty-fourth to thirty-fifth embodiments, wherein the second and third absorbent layers are the same materials.

In a thirty-seventh embodiment, the present disclosure provides the method of any one of the thirty-fourth to thirty-sixth embodiments, wherein the absorbent foam layer comprises polyurethane foam.

In a thirty-eighth embodiment, the present disclosure provides the method of the thirty-seventh embodiment, wherein the polyurethane foam comprises superabsorbent polymer.

In a thirty-ninth embodiment, the present disclosure provides the method of any one of the thirty-fourth to thirty-eighth embodiments, wherein at least one of the second and third absorbent layers comprises superabsorbent polymer sandwiched between two layers of cellulosic fiber tissue.

In a fortieth embodiment, the present disclosure provides the method of any one of the thirty-fourth to thirty-eighth embodiments, wherein at least one of the second and third absorbent layers comprises a preformed fibrous web with superabsorbent polymer dispersed within.

In forty-first embodiment, the present disclosure provides the method of any one of the thirty-fourth to fortieth embodiments, wherein each of the barrier layers comprises at least one of films, coated nonwoven materials, and coated papers.

In a forty-second embodiment, the present disclosure provides the method of any one of the thirty-fourth to the forty-first embodiments, wherein at least one of the barrier layers comprises polyester film.

In a forty-third embodiment, the present disclosure provides the method of any one of the thirty-fourth to forty-first embodiments, wherein at least one of the barrier layers is a film comprising at least one of polypropylene, polyethylene, and co-polymers thereof.

In a forty-fourth embodiment, the present disclosure provides the method of any one of the thirty-fourth to forty-third embodiments, wherein the barrier layers are breached by pin perforation.

In a forty-fifth embodiment, the present disclosure provides the method of any one of the thirty-fourth to forty-third embodiments, wherein the barrier layers are breached by skip slitting.

In a forty-sixth embodiment, the present disclosure provides a method of making an absorbent foam composite comprising taking an intermediate composite comprising an absorbent foam layer having a first side and a second side opposite the first side, a barrier layer having a first side and a second side opposite the first side, where the first side of the barrier layer is joined to the second side of the absorbent foam layer, a second absorbent layer joined to the second side of the barrier layer, a second barrier layer joined to the first side of the absorbent foam layer, where the second barrier layer has a first side and a second side opposite the first side, and the second side of the second barrier layer is in contact with the first side of the absorbent foam layer, and a third absorbent layer joined to the first side of the second barrier layer, wherein the two barrier layers have been breached so that the foam layer is in fluid contact with each of the second and third absorbent layers; and skiving the absorbent foam layer to create two absorbent foam composites.

In a forty-seventh embodiment, the present disclosure provides the method of the forty-sixth embodiment, wherein the two barrier layers are the same materials.

In a forty-eighth embodiment, the present disclosure provides the method of any one of the forty-sixth to forty-seventh embodiments, wherein the second and third absorbent layers are the same materials.

In a forty-ninth embodiment, the present disclosure provides the method of any one of the forty-sixth to forty-eighth embodiments, wherein the absorbent foam layer comprises polyurethane foam.

In a fiftieth embodiment, the present disclosure provides the method of the forty-ninth embodiment, wherein the polyurethane foam comprises superabsorbent polymer.

In a fifty-first embodiment, the present disclosure provides the method of any one of the forty-sixth to fiftieth embodiments, wherein at least one of the second and third absorbent layers comprises superabsorbent polymer sandwiched between two layers of cellulosic fiber tissue.

In a fifty-second embodiment, the present disclosure provides the method of any one of the forty-sixth to fiftieth embodiments, wherein at least one of the second and third absorbent layers comprises a preformed fibrous web with superabsorbent polymer dispersed within.

In a fifty-third embodiment, the present disclosure provides the method of any one of the forty-sixth to fifty-second embodiments, wherein each of the barrier layers comprises at least one of films, coated nonwoven materials, and coated papers.

In a fifty-fourth embodiment, the present disclosure provides the method of any one of the forty-sixth to fifty-third embodiments, wherein at least one of the barrier layers comprises polyester film.

In a fifty-fifth embodiment, the present disclosure provides the method of any one of the forty-sixth to fifty-third embodiments, wherein at least one of the barrier layers is a film comprising at least one of polypropylene, polyethylene, and co-polymers thereof.

In a fifty-sixth embodiment, the present disclosure provides the method of any one of the forty-sixth to fifty-fifth embodiments, wherein the barrier layer is breached by pin perforation.

In a fifty-seventh embodiment, the present disclosure provides the method of any one of the forty-sixth to fifty-fifth embodiments, wherein the barrier layer is breached by skip slitting.

In a fifty-eighth embodiment, the present disclosure provides an intermediate for making an absorbent foam composite comprising an absorbent foam layer having a first side and a second side opposite the first side; a barrier layer having a first side and a second side opposite the first side, where the first side of the barrier layer is joined to the second side of the absorbent foam layer; a second absorbent layer joined to the second side of the barrier layer; a second barrier layer joined to the first side of the absorbent foam layer, where the second barrier layer has a first side and a second side opposite the first side, and the second side of the second barrier layer is in contact with the first side of the absorbent foam layer; and a third absorbent layer joined to the first side of the second barrier layer.

In a fifty-ninth embodiment, the present disclosure provides the intermediate of the fifty-eighth embodiment, wherein the two barrier layers are the same materials.

In sixtieth embodiment, the present disclosure provides the intermediate of any one of the fifty-eighth to fifty-ninth embodiments, wherein the second and third absorbent layers are the same materials.

In sixty-first embodiment, the present disclosure provides the intermediate of any one of the fifty-eighth to sixtieth embodiments, wherein the absorbent foam layer comprises polyurethane foam.

In sixty-second embodiment, the present disclosure provides the intermediate of the sixty-first embodiment, wherein the polyurethane foam comprises superabsorbent polymer.

In sixty-third embodiment, the present disclosure provides the intermediate of any one of the fifty-eighth to sixty-second embodiments, wherein at least one of the second and third absorbent layers comprises superabsorbent polymer sandwiched between two layers of cellulosic fiber tissue.

In sixty-fourth embodiment, the present disclosure provides the intermediate of any one of the fifty-eighth to sixty-second embodiments, wherein at least one of the second and third absorbent layers comprises a preformed fibrous web with superabsorbent polymer dispersed within.

In sixty-fifth embodiment, the present disclosure provides the intermediate of any one of the fifty-eighth to sixty-fourth embodiments, wherein each of the barrier layers comprises at least one of films, coated nonwoven materials, and coated papers.

In sixty-sixth embodiment, the present disclosure provides the intermediate of any one of the fifty-eighth to sixty-fifth embodiments, wherein at least one of the barrier layers comprises polyester film.

In sixty-seventh embodiment, the present disclosure provides the intermediate of any one of the fifty-eighth to sixty-fifth embodiments, wherein at least one of the barrier layers is a film comprising at least one of polypropylene, polyethylene, and co-polymers thereof.

EXAMPLES

The following examples are presented to illustrate some of the advantages of the above method of making an extensible web laminate and are not intended in any way to otherwise limit the scope of the invention.

Ingredients

SUPRASEC® 9561—a modified diphenylmethane diisocyanate (MDI) obtained from Huntsman Chemical Company in The Woodlands, Tex. USA. SUPRASEC® 9561 is reported to have an equivalent weight of 143 g/equivalent, a functionality of 2.10, an isocyanate content of 29.3%, a specific gravity at 25° C. of 1.21, and a viscosity at 25° C. of 36 cps.

CDB-33142—a polyether polyol product obtained from the Carpenter Company in Richmond, Va. USA. CDB-33142 is a blend prepared from glycerine, propylene oxide and ethylene oxide and is reported to have an average Mw of 2300 Da, an average Mn of 1200 Da, an hydroxyl number of 142, a functionality of 3; an ethylene oxide content of 26%; and a viscosity at 25° C. of 500 cps.

ARCOL® E-434—a polyether polyol product obtained from Bayer Material Science in Pittsburgh, Pa. USA. ARCOL® E-434 is prepared as a polyoxy-propylene triol modified with ethylene oxide and is reported to have an average Mw of 4800 Da, a hydroxyl number of 33.8-37.2, and a viscosity at 25° C. of 820 cps.

CARPOL® GP-700—a polyether polyol product obtained from the Carpenter Company in Richmond, Va. USA. CARPOL® GP-700 is a blend prepared from glycerine, propylene oxide, and ethylene oxide and is reported to have an average Mw of 730-770 Da, an average Mn of 700 Da, a hydroxyl number of 240, a functionality of 3, an ethylene oxide content of 0%, and a viscosity at 25° C. of 250 cps.

CARPOL® GP-5171—a polyether polyol product obtained from the Carpenter Company in Richmond, Va. USA.

LiquiBlock™ HS Fines—a superabsorbent polymer (SAP) obtained from Emerging Technologies Inc. in Greensboro, N.C. USA. The SAP is a sodium salt of crosslinked polyacrylic acid and is reported to have a particle size distribution of 1-140 microns, a pH of 6, a NaCl absorption of 50 g/g, a deionized water absorption of >180 g/g, a moisture content of 2% maximum, and an apparent bulk density of 250 g/L.

Triethanolamine LFG (low freeze grade)—obtained from the Dow Chemical Company, Midland, Mich. USA.

DABCO® 33-LV—a solution of triethylene diamine (33 weight percent) in dipropylene glycol obtained from Air Products Company in Allentown, Pa. USA.

DABCO® BL-17—a tertiary amine catalyst obtained from Air Products Company in Allentown, Pa. USA.

DABCO® DC-198—silicone glycol copolymer surfactant obtained from Air Products Company in Allentown, Pa. USA.

DABCO® BA-100—a polymeric acid blocking agent obtained from Air Products Company in Allentown, Pa. USA.

Gelok 5240-72—an absorbent component obtained from Gelok International in Dunbridge, Ohio USA. The absorbent component is a layer of superabsorbent polymer (about 53% by weight of component) sandwiched between two layers of cellulosic fiber tissue (collectively about 47% by weight of component). Each tissue layer has a basis weight of 12 lbs per 300 ft$^2$, where the ream size standard is 500.

Gelok 5240-48—Gelok 5240-72 film laminate obtained from Gelok International in Dunbridge, Ohio USA. One side of the Gelok 5240-72 is adhesively laminated to a 1.0 mil polyester film which contains a heat activatable powder adhesive to facilitate lamination.

Gelok 5240-102—Gelok 5240-72 film laminate obtained from Gelok International in Dunbridge, Ohio USA. One side of the Gelok 5240-72 is polycoated with 3.5 mil polypropylene.

19PP/12PTC1/19PP PERF—polypropylene coated paper available from Prolamina in Neenah, Wis., USA.

MUL/BC 58—polypropylene coated paper obtained from Schoeller Company in Polaski, N.Y., USA.

DispersiTech™ 2226 White—obtained from Milliken in Spartansburg, S.C., USA.

DispersiTech™ 2401 Violet—obtained from Milliken in Spartansburg, S.C., USA.

DispersiTech™ 2425 Blue—obtained from Milliken in Spartansburg, S.C., USA.

DispersiTech™ 2660 Yellow—obtained from Milliken in Spartansburg, S.C., USA.

DispersiTech™ 2800 Red—obtained from Milliken in Spartansburg, S.C., USA.

Pdi® 34-68020 Orange—obtained from Ferro in Cleveland, Ohio, USA.

Test Methods

Composite Thickness. The foam was placed onto a stage and a Keyence model VHX-600E digital stereo microscope (Keyence Corporation, Itasca, Ill.) was rotated 90 degrees in line and centered with the z-plane of the foam. A metric ruler was joined to the stage and adjacent to the z-plane of the foam as a reference. A scale was calibrated using the reference and the sample thickness was measured using ImageJ software. Sample measurements were made in triplicate with the mean value reported.

Basis Weight. A rule die measuring 5.08 cm×5.08 cm (2 inches×2 inches) was used to cut the foam sample for basis weight measurement. The sample was weighed and the basis weight subsequently calculated. Sample measurements were made in triplicate with the mean value reported.

Absorption Capacity. Saline solution (90 ml of 0.9% NaCl in deionized water at room temperature or 21° C.) was poured into a 100 ml disposable Petri dish. A 5.08 cm×5.08 cm (2 inch×2 inch) foam sample was weighed and recorded as "dry weight". The sample was immersed into the Petri dish and allowed to saturate for 5 minutes. The sample was removed by using tweezers to grab a corner of the sample. The sample was suspended vertically for 2 minutes. The wet weight was recorded. The absorption capacity and absorbed fluid were determined as follows:

Absorption Capacity g/g=[(wet sample wt.−dry sample wt.)/dry sample wt.]

Absorption Capacity g/cc=[(wet sample wt.−dry sample wt.)/dry sample volume]

Absorbed Fluid g=wet sample wt.−dry sample wt.

All sample measurements were made in triplicate with the mean value reported.

Strike Through. The strike through time was measured using saline solution and a test jig. The jig was made of plexiglass with the dimensions of 10.16 cm×10.16 cm×2.54 cm (4 inches×4 inches×1 inch). A 2.54 cm hole (1 inch) was cut in the center of the plexiglass jig. The test jig weighed 284 grams. The test sample had a dimension of at least 10.16 cm×10.16 cm. The test sample was placed under the test jig and positioned so that the hole in the plexiglass was directly above the center of the sample. Saline solution (10 mls of 0.9% NaCl in deionized water) was poured into the hole and the time (in seconds) required for the saline solution to penetrate into the test sample was recorded. To enhance visualization, the saline solution was colored with red food dye. The test sample was oriented so that the polyurethane foam layer was in direct contact with the plexiglass surface of the test jig. In this orientation, the polyurethane foam layer was the first surface of the test sample to come in contact with the saline solution. Sample measurements were made in triplicate with the mean value reported.

Rewet. The rewet was determined using the test jig described above for strike through time measurement. The test sample was at least 10.16 cm×10.16 cm. The test sample was placed under the test jig and positioned so that the hole in the plexiglass was directly above the center of the sample. The test samples were oriented so that the polyurethane foam layer was in direct contact with the plexiglass surface of the test jig. In this orientation, the polyurethane foam layer was the first surface of the test sample to come in contact with the saline solution. Saline (10 ml of 0.9% NaCl in deionized water) was poured into the hole and the sample was maintained in the test jig for 5 minutes. The load was 0.28 kPa (0.04 psi). The test jig was removed and a stack of ten sheets of WHATMAN #4 90 mm filter paper was placed on top of the test sample. Prior to placement on the sample, the stack of filter paper was weighed to obtain an initial weight. The test jig, weighing 284 grams, was reapplied to the sample and a 2200 gram weight (Examples 1-3 and Comparative Example 1) or 2000 gram weight (Examples 4-8 and Comparative Examples 4 & 7) was placed and centered on top of the plexiglass test jig, providing a loading of 3.827 kPa (0.56 psi) or 3.52 kPa (0.51 psi), respectively, for 15 seconds. The assembly was removed and the stack of filter paper weighed again to obtain a final weight. The rewet measurement was calculated using the following equation:

Rewet (g)=final filter paper weight−initial filter paper weight.

All samples were made in triplicate and reported as the mean value.

Example 1

An open cell polyurethane foam was prepared by adding SUPRASEC® 9561 (61.0 parts, 29.59 wt. %) to a mixture of CDB-33142 (100 parts, 48.5 wt. %), LiquiBlock™ HS Fines (30 parts, 14.55 wt. %), CARPOL® GP-700 (3.6 parts, 1.75 wt. %), water (1.2 parts, 0.58 wt. %), triethanolamine LFG (3.7 parts, 1.79 wt. %), DABCO® DC-198 (2.0 parts, 0.97 wt. %), ARCOL® E-434 (4.0 parts, 1.94 wt. %), DABCO® 33 LV (0.45 parts, 0.22 wt. %), DABCO® BL-17 (0.10 parts, 0.05 wt. %) and DABCO® BA 100 (0.12 parts, 0.06 wt. %), and casting the combination of foam ingredients onto the polyester film side of Gelok 5240-48. MUL/BC 58 polypropylene coated release paper was applied to the opposite side of the foam as it was conveyed between a pair of metering rolls. The foam was cured in an oven at 100° C. for 5 minutes. After curing, the release paper was stripped from the composite and the composite was pin perforated to breach the polyester film layer.

Perforation was carried out with a hand-held pin perforating wheel having a pin density of 112 pins/in$^2$. The pins were 21 gauge tapered and the pin exposed length was 4.5 mm (0.177 inches). Such a perforating device is available, for example, from Stewarts of America in Simpsonville, S.C. USA. The foam composite was perforated by laying the composite on a compliant rubber mat and rolling the perforating wheel over the top of the composite. The rubber mat minimized damage to the tips of the pins.

The absorbent foam composite had an average thickness of 3.3 mm, an average basis weight of 445 gsm, an average total composite density of 0.1348 g/cc (8.41 pcf), an average strike through of 2.2 seconds, an average rewet of 0.33 grams, an average absorbed fluid of 14.43 grams, and an average absorption capacity of 12.57 g/g (1.69 g/cc).

Comparative Example 1

An open cell polyurethane foam was prepared by adding SUPRASEC® 9561 (61.0 parts, 29.59 wt. %) to a mixture of CDB-33142 (100 parts, 48.5 wt. %), LiquiBlock™ HS Fines (30 parts, 14.55 wt. %), CARPOL® GP-700 (3.6 parts, 1.75 wt. %), water (1.2 parts, 0.58 wt. %), triethanolamine LFG (3.7 parts, 1.79 wt. %), DABCO® DC-198 (2.0 parts, 0.97 wt. %), ARCOL® E-434 (4.0 parts, 1.94 wt. %), DABCO® 33 LV (0.45 parts, 0.22 wt. %), DABCO® BL-17 (0.10 parts, 0.05 wt. %), DABCO® BA 100 (0.12 parts, 0.06 wt. %), and casting the combination of foam ingredients onto a modified Gelok 5240-72, where one of the two tissues is replaced by an 18 lb tissue (ream size standard is 500) and the foam ingredients are deposited on the 18 lb tissue side. MUL/BC 58 polypropylene coated release paper was applied to the opposite side of the foam as it was conveyed between a pair of metering rolls. The foam was cured in an oven at 100° C. for 5 minutes. After curing, the release paper was stripped from the composite.

The absorbent foam composite had an average thickness of 3.3 mm, an average basis weight of 383 gsm, an average total composite density of 0.1160 g/cc (7.23 pcf), an average strike through of 3.6 seconds, an average rewet of 4.04 grams, an average absorbed fluid of 8.66 grams, and an average absorption capacity of 8.77 g/g (1.02 g/cc).

Example 2

An open cell polyurethane foam was prepared by adding SUPRASEC® 9561 (62.2 parts, 29.88 wt. %) to a mixture of CDB-33142 (100 parts, 48.04 wt. %), LiquiBlock™ HS Fines (30 parts, 14.41 wt. %), CARPOL® GP 5171 (5.4 parts, 2.59 wt. %), water (1.2 parts, 0.58 wt. %), triethanolamine LFG (3.7 parts, 1.78 wt. %), DABCO® DC-198 (1.0 parts, 0.48 wt. %), ARCOL® E-434 (4.0 parts, 1.92 wt. %), DABCO® 33 LV (0.45 parts, 0.22 wt. %), DABCO® BL-17 (0.10 parts, 0.05 wt. %), and DABCO® BA 100 (0.12 parts, 0.06 wt. %), and casting the combination of foam ingredients onto the polyester film side of Gelok 5240-48. MUL/BC 58 polypropylene coated release paper was applied to the opposite side of the foam as it was conveyed between a pair of metering rolls. The foam was cured in an oven at 116° C. (240° F.) for 3.0 minutes. After curing, the release paper was stripped from the composite and the composite was pin perforated to breach the polyester film layer.

Perforation was carried out with a hand-held pin perforating wheel having a pin density of 270 pins/in². The pins were 21 gauge tapered and the pin exposed length was 4.5 mm (0.177 inches). Such a perforating device is available, for example, from Stewart of America in Simpsonville, S.C. USA. The foam composite was perforated by laying the composite on a compliant rubber mater and rolling the perforating wheel over the top of the composite. The rubber mat minimized damage to the tips of the pins.

The open cell foam had an average thickness of 3.0 mm, an average basis weight of 281 gsm, and average density of 0.0924 g/cc (5.76 pcf).

The absorbent foam composite had an average thickness of 3.3 mm, an average basis weight of 402 gsm, and an average composite density of 0.1202 g/cc (7.50 pcf). The absorbent foam composite also had an average strike through of 4.3 seconds and an average rewet of 0.47 grams.

Example 3

An open cell polyurethane foam was prepared by adding SUPRASEC® 9561 (62.2 parts, 29.88 wt. %) to a mixture of CDB-33142 (100 parts, 48.04 wt. %), LiquiBlock™ HS Fines (30 parts, 14.41 wt. %), CARPOL® GP 5171 (5.4 parts, 2.59 wt. %), water (1.2 parts, 0.58 wt. %), triethanolamine LFG (3.7 parts, 1.78 wt. %), DABCO® DC-198 (1.0 parts, 0.48 wt. %), ARCOL® E-434 (4.0 parts, 1.92 wt. %), DABCO® 33 LV (0.45 parts, 0.22 wt. %), DABCO® BL-17 (0.10 parts, 0.05 wt. %), DABCO® BA 100 (0.12 parts, 0.06 wt. %), and casting the combination of foam ingredients onto the polyester film side of the Gelok 5240-48. In place of a release paper, the polyester film side of a second strip of Gelok 5240-48 was applied to the opposite side of the foam as it passed between a pair of metering rolls, such that the foam was sandwiched between two strips of Gelok 5420-48. The foam was cured in an oven at 116° C. for 3.0 minutes.

The foam composite was skived through the center of the foam layer to create two nearly equally constructed foam composites. Such skiving equipment is available, for example, from Baumer of America, Inc., in Towaco, N.J., USA.

The foam composite was then pin perforated to breach the polyester film layers. Perforation was carried out with a hand-held pin perforating wheel having a pin density of 112 pins/in². The pins were 21 gauge tapered and the pin exposed length was 4.5 mm (0.177 inches). Such a perforating device is available, for example, from Stewart of America in Simpsonville, S.C. USA. The foam composite was perforated by laying the composite on a compliant rubber mater and rolling the perforating wheel over the top of the composite. The rubber mat minimized damage to the tips of the pins.

The foam composite before skiving had an average thickness of 7.5 mm, an average basis weight of 890 gsm, and an average composite density of 0.1192 g/cc (7.44 pcf). The Gelok 5240-48 had an average thickness of 0.27 mm and an average basis weight of 109 gsm. The foam layer had an average thickness of 6.9 mm, an average basis weight of 671 gsm, and an average density of 0.0973 g/cc (6.07 pcf).

After skiving, one of the two foam composites had an average thickness of 2.7 mm, an average basis weight of 350 gsm, and an average density of 0.1296 g/cc (8.08 pcf).

After perforating the foam composite, the resultant absorbent foam composite had an average strike through of 4.9 seconds, an average rewet of 0.12 grams, an average absorbed fluid of 14.74 grams, and an average absorption capacity of 16.09 g/g (2.12 g/cc).

Example 4

An open cell polyurethane foam was prepared by adding SUPRASEC® 9561 (65.0 parts, 33.85 wt. %) to a mixture of CDB-33142 (100 parts, 52.08 wt. %), LiquiBlock™ HS Fines (13 parts, 6.77 wt. %), CARPOL® GP-5171 (6.6 parts, 3.44 wt. %), water (2.2 parts, 1.15 wt. %), triethanolamine LFG (3.7 parts, 1.93 wt. %), DABCO® DC-198 (1.0 parts, 0.52 wt. %), DABCO® 33 LV (0.35 parts, 0.18 wt. %), DABCO® BL-17 (0.08 parts, 0.04 wt. %) and DABCO® BA 100 (0.10 parts, 0.05 wt. %), and casting the combination of foam ingredients onto the polyester film side of Gelok 5240-48. 19PP/12PTC1/19PP PERF polypropylene coated release paper was applied to the opposite side of the foam as it was conveyed between a pair of metering rolls. The foam was cured in an oven at 116° C. (250° F.) for 2.25 minutes. After curing, the release paper was stripped from the composite and the composite was skip slit to breach the polyester film layer.

Skip slitting was carried out with a stainless steel anvil nip roll against a stainless steel patterned cutting die roll having a 5-2-2 skip slit pattern. The first digit represents the slit length in mm. The second digit represents the distance in mm between slits in the machine direction. The third digit represents the distance in mm between slits in the cross direction. The adjacent skip slit row is offset by ½ times the repeat length. This sequence is repeated across the entire cross direction of the roll.

The open cell foam had an average thickness of 2.53 mm, an average basis weight of 164.4 gsm, and an average density of 0.0650 g/cc (4.06 pcf).

The absorbent foam composite had an average thickness of 2.8 mm, an average basis weight of 283.4 gsm, and an average density of 0.1000 g/cc (6.24 pcf). The absorbent foam composite also had an average strike through of 2.8 seconds, an average rewet of 0.22 grams, an average absorbed fluid of 11.73 grams, and an average absorption capacity of 16.42 g/g (1.95 g/cc).

Comparative Example 4

The absorbent foam composite in Example 4 was tested prior to skip slitting. The comparative absorbent foam composite had an average strike through of 4.6 seconds, an average rewet of 7.55 grams, and an average absorption capacity of 14.84 g/g (1.72 g/cc).

Example 5

An open cell polyurethane foam was prepared by adding SUPRASEC® 9561 (65.0 parts, 33.85 wt. %) to a mixture of CDB-33142 (100 parts, 52.08 wt. %), LiquiBlock™ HS Fines (13 parts, 6.77 wt. %), CARPOL® GP-5171 (6.60 parts, 3.44 wt. %), water (2.2 parts, 1.15 wt. %), triethanolamine LFG (3.7 parts, 1.93 wt. %), DABCO® DC-198 (1.0 parts, 0.52 wt. %), DABCO® 33 LV (0.35 parts, 0.18 wt. %), DABCO® BL-17 (0.08 parts, 0.04 wt. %) and DABCO® BA 100 (0.10 parts, 0.05 wt. %), and casting the combination of foam ingredients onto the polyester film side of Gelok 5240-48. 19PP/12PTC1/19PP PERF polypropylene coated release paper was applied to the opposite side of the foam as it was conveyed between a pair of metering rolls. The foam was cured in an oven at 116° C. (250° F.) for 2.25 minutes. After curing, the release paper was stripped from the composite and the composite was pin perforated to breach the polyester film layer.

Perforation was carried out with a hand-held pin perforating wheel having a pin density of 112 pins/in$^2$. The pins were 21 gauge tapered and the pin exposed length was 4.5 mm (0.177 inches). Such a perforating device is available, for example, from Stewart of America in Simpsonville, S.C. USA. The foam composite was perforated by laying the composite on a compliant rubber mater and rolling the perforating wheel over the top of the composite. The rubber mat minimized damage to the tips of the pins.

The open cell foam had an average thickness of 2.53 mm, an average basis weight of 164.4 gsm, and an average density of 0.0650 g/cc (4.06 pcf).

The absorbent foam composite had an average thickness of 2.8 mm, an average basis weight of 283.4 gsm, and an average density of 0.1000 g/cc (6.24 pcf). The absorbent foam composite also had an average strike through of 2.7 seconds, an average rewet of 0.26 grams, an average absorbed fluid of 12.17 grams, and an average absorption capacity of 16.30 g/g (1.86 g/cc).

Example 6

An open cell polyurethane foam was prepared by adding SUPRASEC® 9561 (66.7 parts, 34.61 wt. %) to a mixture of CDB-33142 (100 parts, 51.89 wt. %), LiquiBlock™ HS Fines (13 parts, 6.75 wt. %), CARPOL® GP-5171 (5.85 parts, 3.04 wt. %), water (1.95 parts, 1.01 wt. %), triethanolamine LFG (3.7 parts, 1.92 wt. %), DABCO® DC-198 (1.0 parts, 0.52 wt. %), DABCO® 33 LV (0.35 parts, 0.18 wt. %), DABCO® BL-17 (0.08 parts, 0.04 wt. %) and DABCO® BA 100 (0.10 parts, 0.05 wt. %), and casting the combination of foam ingredients onto the polypropylene film side of Gelok 5240-102. 19PP/12PTC1/19PP PERF polypropylene coated release paper was applied to the opposite side of the foam as it was conveyed between a pair of metering rolls. The foam was cured in an oven at 116° C. (250° F.) for 2.25 minutes. After curing, the release paper was stripped from the composite and the composite was pin perforated to breach the polypropylene film layer.

Perforation was carried out with a hand-held pin perforating wheel having a pin density of 112 pins/in$^2$. The pins were 21 gauge tapered and the pin exposed length was 4.5 mm (0.177 inches). Such a perforating device is available, for example, from Stewart of America in Simpsonville, S.C. USA. The foam composite was perforated by laying the composite on a compliant rubber mater and rolling the perforating wheel over the top of the composite. The rubber mat minimized damage to the tips of the pins.

The open cell foam had an average thickness of 2.44 mm, an average basis weight of 187.4 gsm, and an average density of 0.0768 g/cc (4.79 pcf).

The absorbent foam composite had an average thickness of 2.7 mm, an average basis weight of 302.7 gsm, and an average density of 0.1103 g/cc (6.88 pcf). The absorbent foam composite also had an average strike through of 5.5 seconds, an average rewet of 0.22 grams, an average absorbed fluid of 8.90 grams, and an average absorption capacity of 11.42 g/g or 1.44 g/cc.

Example 7

An open cell polyurethane foam was prepared by adding SUPRASEC® 9561 (63.4 parts, 35.77 wt. %) to a mixture of CDB-33142 (100 parts, 56.42 wt. %), CARPOL® GP-5171 (5.7 parts, 3.22 wt. %), water (1.9 parts, 1.07 wt. %), triethanolamine LFG (3.7 parts, 2.09 wt. %), DABCO® DC-198 (1.0 parts, 0.56 wt. %), DABCO® 33 LV (0.35 parts, 0.20 wt. %), DABCO® BL-17 (0.08 parts, 0.05 wt. %) and DABCO® BA 100 (0.10 parts, 0.06 wt. %), and casting the combination of foam ingredients onto the polyester film side of Gelok 5240-48. 19PP/12PTC1/19PP PERF polypropylene coated release paper was applied to the opposite side of the foam as it was conveyed between a pair of metering rolls. The foam was cured in an oven at 116° C. (250° F.) for 2.25 minutes. After curing, the release paper was stripped from the composite and the composite was skip slit to breach the polyester film layer.

Skip slitting was carried out with a stainless steel anvil nip roll against a stainless steel patterned cutting die roll having a 5-2-2 skip slit pattern. The first digit represents the slit length in mm. The second digit represents the distance in mm between slits in the machine direction. The third digit represents the distance in mm between slits in the cross direction. The adjacent skip slit row is offset by ½ times the repeat length. This sequence is repeated across the entire cross direction of the roll.

The open cell foam had an average thickness of 2.43 mm, an average basis weight of 145.9 gsm, and an average density of 0.0601 g/cc (3.75 pcf).

The absorbent foam composite had an average thickness of 2.7 mm, an average basis weight of 267.6 gsm, and an average density of 0.0980 g/cc (6.11 pcf). The absorbent foam composite also had an average strike through of 3.8 seconds, an average rewet of 0.73 grams, an average absorbed fluid of 10.74 grams, and an average absorption capacity of 14.04 g/g (1.47 g/cc).

Comparative Example 7

The absorbent foam composite in Example 7 was tested prior to skip slitting. The comparative absorbent foam composite had an average strike through of 9.1 seconds, an average rewet of 9.32 grams, an average absorbed fluid of 9.77, and an average absorption capacity of 12.09 g/g (1.40 g/cc).

Example 8

An open cell polyurethane foam was prepared by adding SUPRASEC® 9561 (63.4 parts, 35.77 wt. %) to a mixture of CDB-33142 (100 parts, 56.42 wt. %), CARPOL®

GP-5171 (5.7 parts, 3.22 wt. %), water (1.9 parts, 1.07 wt. %), triethanolamine LFG (3.7 parts, 2.09 wt. %), DABCO® DC-198 (1.0 parts, 0.56 wt. %), ARCOL® E-434 (1.0 parts, 0.56 wt. %), DABCO® 33 LV (0.35 parts, 0.20 wt. %), DABCO® BL-17 (0.08 parts, 0.05 wt. %) and DABCO® BA 100 (0.10 parts, 0.06 wt. %), and casting the combination of foam ingredients onto the polyester film side of Gelok 5240-48. 19PP/12PTC1/19PP PERF polypropylene coated release paper was applied to the opposite side of the foam as it was conveyed between a pair of metering rolls. The foam was cured in an oven at 116° C. (250° F.) for 2.25 minutes. After curing, the release paper was stripped from the composite and the composite was pin perforated to breach the polyester film layer.

Perforation was carried out with a hand-held pin perforating wheel having a pin density of 112 pins/in$^2$. The pins were 21 gauge tapered and the pin exposed length was 4.5 mm (0.177 inches). Such a perforating device is available, for example, from Stewart of America in Simpsonville, S.C. USA. The foam composite was perforated by laying the composite on a compliant rubber mater and rolling the perforating wheel over the top of the composite. The rubber mat minimized damage to the tips of the pins.

The open cell foam had an average thickness of 2.43 mm, an average basis weight of 145.9 gsm, and an average density of 0.0601 g/cc (3.75 pcf).

The absorbent foam composite had an average thickness of 2.7 mm, an average basis weight of 267.6 gsm, and an average density of 0.0980 g/cc (6.11 pcf). The absorbent foam composite also had an average strike through of 4.4 seconds, an average rewet of 0.63 grams, an average absorbed fluid of 11.34, and an average absorption capacity of 15.01 g/g (1.76 g/cc).

Example 9

Colored open cell polyurethane foams 9A-F were prepared by adding SUPRASEC® 9561 (59.5 parts) to a mixture of CDB-33142 (100 parts), LiquiBlock™ HS Fines (30 parts), CARPOL® GP 700 (3.6 parts), water (1.2 parts), triethanolamine LFG (3.7 parts), DABCO® DC-198 (2.0 parts), ARCOL® E-434 (4.0 parts), DABCO® 33 LV (0.45 parts), DABCO® BA 100 (0.12 parts), DABCO® BL-17 (0.10 parts) and colorant as specified in Table 1 below, and curing at 100° C. for 10 minutes.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention.

Thus, the invention provides, among other things, a method of making an absorbent foam composite and absorbent foam composites produced therefrom. Various features and advantages of the invention are set forth in the following claims.

What is claimed is:

1. A method of making an absorbent foam composite comprising:
    casting an hydrophilic open-celled absorbent foam layer having a first side and a second side opposite the first side onto a barrier layer having a first side and a second side opposite the first side, where the second side of the absorbent foam layer is in contact with the first side of the barrier layer;
    joining a second absorbent layer to the second side of the barrier layer before, during, or after the casting step; and
    breaching the barrier layer after the casting step so that the absorbent foam layer and second absorbent layer are in fluid communication.

2. The method of claim 1, wherein the absorbent foam layer comprises polyurethane foam.

3. The method of claim 1, wherein the second absorbent layer comprises superabsorbent polymer sandwiched between two layers of cellulosic fiber tissue.

4. The method of claim 1, wherein the second absorbent layer comprises a preformed fibrous web with superabsorbent polymer dispersed within.

5. The method of claim 1, wherein the barrier layer comprises at least one of films, coated nonwoven materials, and coated papers.

6. The method of claim 1, wherein the barrier layer comprises polyester film.

7. The method of claim 1, wherein the barrier layer is a film comprising at least one of polypropylene, polyethylene, and co-polymers thereof.

8. The method of claim 1, wherein the barrier layer is breached by pin perforation.

9. The method of claim 1, wherein the barrier layer is breached by skip slitting.

TABLE 1

|  | Ex. 9A Yellow | Ex. 9B Orange | Ex. 9C Blue | Ex. 9D Violet | Ex. 9E Red | Ex. 9F Lavender |
|---|---|---|---|---|---|---|
| DispersiTech ™ 2660 Yellow | 2.0 parts | | | | | |
| Pdi ® 34-68020 Orange | | 2.0 parts | | | | |
| DispersiTech ™ 2425 Blue | | | 2.0 parts | | | |
| DispersiTech ™ 2401 Violet | | | | 2.0 parts | | |
| DispersiTech ™ 2800 Red | | | | | 2.0 parts | |
| DispersiTech ™ 2401 Violet | | | | | | 0.4 parts |
| DispersiTech ™ 2226 White | | | | | | 1.0 parts |

10. A method of making an absorbent foam composite comprising:
- casting an hydrophilic open-celled absorbent foam layer having a first side and a second side opposite the first side onto a barrier layer having a first side and a second side opposite the first side, where the second side of the absorbent foam layer is in contact with the first side of the barrier layer;
- joining a second absorbent layer to the second side of the barrier layer before, during, or after the casting step;
- adding a second barrier layer to the first side of the absorbent foam layer during the casting step, where the second barrier layer has a first side and a second side opposite the first side, and the second side of the second barrier layer is in contact with the first side of the absorbent foam layer;
- joining a third absorbent layer to the first side of the second barrier layer before, during or after the casting step;
- breaching the two barrier layers so that the absorbent foam layer is in fluid contact with each of the second and third absorbent layers; and
- skiving the foam layer to create two absorbent foam composites.

11. The method of claim 10, wherein the absorbent foam layer comprises polyurethane foam.

* * * * *